United States Patent [19]

Braestrup et al.

[11] Patent Number: 4,596,808
[45] Date of Patent: Jun. 24, 1986

[54] PHARMACOLOGICALLY ACTIVE 3-SUBSTITUTED BETA-CARBOLINES USEFUL AS TRANQUILIZERS

[75] Inventors: Claus T. Braestrup, Gentofte; Jogen A. Christensen, Virum; Mogens Engelstoft, Vaerloese, all of Denmark; Guenter Neef, Berlin, Fed. Rep. of Germany; Ulrich Eder, Berlin, Fed. Rep. of Germany; Ralph Schmiechen, Berlin, Fed. Rep. of Germany; Andreas Huth, Berlin, Fed. Rep. of Germany; Dieter Rahtz, Berlin, Fed. Rep. of Germany; Dieter Seidelmann, Berlin, Fed. Rep. of Germany; Wolfgang Kehr, Berlin, Fed. Rep. of Germany; Dieter Palenschat, Berlin, Fed. Rep. of Germany

[73] Assignee: Schering Aktiengesellschaft, Berlin and Bergkanes, Fed. Rep. of Germany

[21] Appl. No.: 556,869

[22] Filed: Dec. 1, 1983

Related U.S. Application Data

[63] Continuation-in-part of Ser. No. 331,740, Dec. 17, 1981, Pat. No. 4,435,403.

[30] Foreign Application Priority Data

Dec. 17, 1980 [DE] Fed. Rep. of Germany ....... 3048318
Feb. 27, 1981 [DK] Denmark ............................... 913/81
Sep. 14, 1981 [DE] Fed. Rep. of Germany ....... 3136857

[51] Int. Cl.$^4$ ................. C07D 487/14; A61K 31/435
[52] U.S. Cl. ..................................... 514/292; 546/85; 546/86; 546/87
[58] Field of Search .................... 546/86, 87; 424/256; 514/292

[56] References Cited

U.S. PATENT DOCUMENTS 4,371,536  2/1983  Braestrup et al. ................... 514/292

Primary Examiner—Alan L. Rotman
Attorney, Agent, or Firm—Millen & White

[57] ABSTRACT

3-Substituted beta-carbolines of the formula

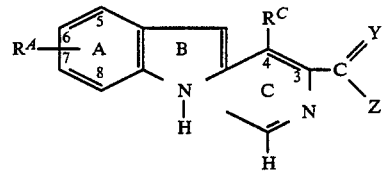

wherein
$R^A$ is H, F, Cl, Br, I, $NO_2$, CN, $CH_3$, $CF_3$, $SCH_3$, $NR^{16}R^{17}$ or $NHCOR^{16}$,
  wherein $R^{16}$ and $R^{17}$ are the same or different and each is hydrogen or alkyl, alkenyl or alkynyl each of up to 6 C-atoms, aralkyl or cycloalkyl each of up to 10 C-atoms,
  or wherein $R^{16}$ and $R^{17}$ together form a saturated or unsaturated 3–7 membered heterocyclic ring;

said compounds possess valuable psychotropic properties which make them useful for example as tranquilizers.

26 Claims, No Drawings

PHARMACOLOGICALLY ACTIVE 3-SUBSTITUTED BETA-CARBOLINES USEFUL AS TRANQUILIZERS

CROSS REFERENCE TO RELATED APPLICATION

This application is a continuation-in-part application of U.S. Ser. No. 331,740 filed on Dec. 17, 1981, now U.S. Pat. No. 4,435,403 issued Mar. 6, 1984.

BACKGROUND OF THE INVENTION

The present invention relates to new 3-substituted beta-carbolines, a process for preparing them and their uses.

Canadian Pat. No. 786,351 describes beta-carboline-3-carboxylic acid amides which are substituted in the 1-position by alkyl of up to 5 C-atoms, trifluoromethyl, phenyl or benzyl, as well as two specific compounds without substituents in the 1-position, namely beta-carboline-3-carbohydrazide and beta-carboline-3-carboxylic acid amide. Additionally, other 1-unsubstituted amides are disclosed generically.

Danish Pat. No. 98 436 describes a process for preparing beta-carboline-3-carboxylic-acid methylester.

SUMMARY OF THE INVENTION

It is an object of this invention to provide new 3-substituted-β-carbolines having useful pharmacological properties.

Upon further study of the specification and appended claims, further objects and advantages of this invention will become apparent to those skilled in the art.

These objects have been attained by providing 3-substituted beta-carbolines of formula I,

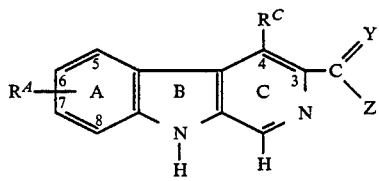

wherein
$R^A$ is H, F, Cl, Br, I, $NO_2$, CN, $C_{1-3}$-alkyl, $CF_3$, $SCH_3$, $NR^{16}R^{17}$ or $NHCOR^{16}$,
  wherein $R^{16}$ and $R^{17}$ are the same or different and each is hydrogen or alkyl, akenyl or alkynyl each of up to 6 C-atoms, aralkyl or cycolalkyl each of up to 10 C-atoms,
    all of which groups for $R^{16}$ and $R^{17}$, except for H, can optionally be substituted by halogen, hydroxy, SH, $SR^{23}$, $COOR^{23}$, nitrilo, $CONR^{23}R^{24}$, $CHOR^{23}OR^{24}$ or $CHSR^{23}SR^{24}$,
      wherein $R^{23}$ and $R^{24}$ are the same or different and each is hydrogen or a lower alkyl of up to 3 C-atoms,
  or wherein $R^{16}$ and $R^{17}$ together form a saturated or unsaturated 3-7 membered heterocyclic ring, optionally substituted with a lower alkyl group of up to 3 C-atoms, $=S$, $=O$, $OR^{23}$, $SR^{23}$ or $NR^{23}R^{24}$, wherein a C-atom in the hetero ring may optionally be replaced by S, O or $NR^{23}$; wherein, throughout, $R^{23}$ is as defined above;
or $R^A$ is

wherein $R^{23}$ and $R^{24}$ are the same or different and each is as defined above;
or $R^A$ is $CHR^{33}$—$OR^{39}$, wherein $R^{33}$ and $R^{39}$ are the same or different and $R^{33}$ is hydrogen or lower alkyl of up to 3 C-atoms and $R^{39}$ is hydrogen, lower alkyl of up to 3 C-atoms or

or $R^A$ is $OR^{18}$ wherein $R^{18}$ is alkyl, aryl or aralkyl each of up to 12 C-atoms;
or $R^A$ is $C\equiv CR^{35}$,
  wherein $R^{35}$ is hydrogen, lower alkyl of up to 3 C-atoms, aryl of up to 12 C atoms, or $CHR^{33}R^{30}$,
    wherein $R^{33}$ is as defined above and $R^{30}$ is halogen, $OR^{40}$ or $NR^{41}R^{42}$,
      wherein $R^{40}$ is hydrogen, lower alkyl of up to 3 C-atoms, or $C_4$ or 5-alkylene thereby forming a 5- or 6-membered heterocyclic ring containing O and wherein $R^{41}$ and $R^{42}$ are the same or different and each is hydrogen or lower alkyl, or together are $C_4$ or 5-alkylene forming a ring with the N-atom,
  or $R^{35}$ is

wherein $R^{23}$ and $R^{24}$ are as defined above;
or $R^A$ is $COOR^2$, $SR^2$ or $SO_2R^2$, wherein $R^2$ is alkyl of up to 6 C atoms;
or $R^A$ is $SO_2NR^{21}R^{22}$ wherein $R^{21}$ and $R^{22}$ each is H or lower alkyl,
and wherein each compound may contain 1–4 identical or different non-H $R^A$ groups;
$R^C$ is hydrogen, lower alkyl, alkoxyalkyl of up to 6 C-atoms, cycloalkyl of 3–6 C-atoms, aralkyl of up to 8 C-atoms, or $(CH_2)_nOR^{20}$
  wherein $R^{20}$ is alkyl of up to 6 C-atoms, cycloalkyl of 3–6 C-atoms or aralkyl of up to 8 C-atoms and n is an integer of 1 to 3;
Y is oxygen, two hydrogen atoms or $NOR^1$,
  wherein $R^1$ is hydrogen, lower alkyl, aryl or aralkyl of up to 6 C-atoms, $COR^2$, wherein $R^2$ is lower alkyl of up to 6 C-atoms,
or Y is $CHCOOR^3$, wherein $R^3$ is hydrogen or lower alkyl
or Y is $NNR^4R^5$,
  wherein $R^4$ and $R^5$ can be the same or different and each is hydrogen, lower alkyl, $C_{6-10}$-aryl, $C_{7-10}$-aralkyl or $CONR^6R^7$,
    wherein $R^6$ and $R^7$ can be the same or different and each is hydrogen or lower alkyl or $R^4$ and $R^5$ together with the connecting N-atom, for a 5- or 6-membered heterocyclic ring which optionally may also contain an O-atom or up to 3 N-atoms and which optionally may be substituted by a lower alkyl group;

Z is hydrogen, or alkoxy or aralkoxy each of up to 10 C-atoms and each optionally substituted by hydroxy, or Z is alkyl of up to 6 C-atoms, $C_{6-10}$-aryl or $C_{7-10}$-aralkyl each of which may optionally be substituted by a $COOR^8$— or a $CONR^9R^{10}$ group, wherein $R^8$ is alkyl of up to 6 C-atoms, and $R^9$ and $R^{10}$ can be the same or different and each is hydrogen or alkyl of up to 6 C-atoms;

or Z is $NR^9R^{10}$, wherein $R^9$ and $R^{10}$ are as defined above;

or Z is $NR^{11}CHR^{12}R^{13}$, wherein $R^{11}$ and $R^{12}$ each is hydrogen or together form a N=C double bond, wherein $R^{13}$ is $C_{1-10}$-alkyl or $NR^{14}R^{15}$, wherein $R^{14}$ and $R^{15}$ are the same or different and each is hydrogen, OH or alkyl or alkoxy each of up to 6 C-atoms, or wherein $R^{12}$ and $R^{13}$ together are oxygen, in which case, $R^{11}$ is hydrogen;

or Z is $COOR^2$ wherein $R^2$ is as defined above;

or Y and Z, together with the connecting C-atom, may form a 5- or 6-membered heterocyclic ring which contains an O-atom, adjoining O- and N-atoms or up to 4N atoms and which optionally may be substituted by a lower alkyl group, hydroxy or oxo.

Insofar as compounds effectively disclosed in U.S. application Ser. No. 182,244 are included in the above, they are not part of this invention.

This invention particularly relates to those compounds above wherein Y is not oxygen. When Y is oxygen, it particularly relates to (1) those compounds wherein $R^A$ and $R^C$ are as defined above and Z is hydrogen; alkyl of up to 6 C-atoms, $C_{6-10}$-aryl or $C_{7-10}$-aralkyl each of which may optionally be substituted by a $COOR^8$- or a $CONR^9R^{10}$ group, wherein $R^8$ is alkyl of up to 6 C-atoms, and $R^9$ and $R^{10}$ can be the same or different and each is hydrogen or alkyl of up to 6 C-atoms;

or Z is $NR^{11}CHR^{12}R^{13}$, wherein $R^{11}$ and $R^{12}$ together represent an N=C double bond, wherein $R^{13}$ is $C_{1-10}$-alkyl or $NR^{14}R^{15}$ wherein $R^{14}$ and $R^{15}$ are the same or different and each is hydrogen, OH or alkyl or alkoxy each of up to 6 C-atoms, or $R^{12}$ and $R^{13}$ together are oxygen, in which case, $R^{11}$ is hydrogen; or $R^{11}$ and $R^{12}$ are both H wherein $R^{13}$ is $NR^{14}R^{15}$ wherein $R^{14}$ and $R^{15}$ are the same or different and each is OH or $C_{1-6}$-alkoxy;

or Z is $COOR^2$ wherein $R^2$ is as defined above.

(2) those compounds wherein $R^C$ is as defined above, Z is alkoxy or aralkoxy each of up to 10 C-atoms, and each optionally substituted by hydroxy;

or Z is $NR^9R^{10}$, wherein $R^9$ and $R^{10}$ each independently is H or $C_{1-6}$-alkyl;

or Z is $NR^{11}CHR^{12}R^{13}$, wherein $R^{11}$ and $R^{12}$ each is hydrogen and $R^{13}$ is alkyl or $NR^{14}R^{15}$ wherein $R^{14}$ and $R^{15}$ are the same or different and each is hydrogen or alkyl;

and $R^A$ is $CH_3$, $CF_3$, $SCH_3$, $NR^{16}R^{17}$ or $NHCOR^{16}$, wherein $R^{16}$ and $R^{17}$ are the same or different and each is alkenyl or alkynyl each of up to 6 C-atoms, aralkyl or cycloalkyl each of up to 10 C-atoms, all of which groups for $R^{16}$ and $R^{17}$, except for H, can optionally be substituted by SH, $SR^{23}$, $COOR^{23}$, nitrilo, $CONR^{23}R^{24}$, $CHOR^{23}OR^{24}$ or $CHSR^{23}SR^{24}$, wherein $R^{23}$ and $R^{24}$ are the same or different and each is hydrogen or a lower alkyl of up to 3 C atoms, or whereby $R^{16}$ and $R^{17}$ together form a saturated or unsaturated 3-7 membered heterocyclic ring, optionally substituted with a lower alkyl group of up to 3 C-atoms, =C, =O, $OR^{23}$, $SR^{23}$ or $NR^{23}R^{24}$, wherein a C-atom in the hetero ring may optionally be replaced by S, O or $NR^{23}$;

wherein, throughout, $R^{23}$ is as defined above;

or $R^A$ is

wherein $R^{23}$ and $R^{24}$ are the same or different and each is as defined above;

or $R^A$ is $CHR^{33}$—$OR^{39}$, wherein $R^{33}$ and $R^{39}$ are the same or different and $R^{33}$ is hydrogen or lower alkyl of up to 3 C-atoms and $R^{39}$ is hydrogen, lower alkyl of up to 3 C-atoms or

or $R^A$ is $OR^{18}$ wherein $R^{18}$ is aryl or aralkyl each of up to 12 C-atoms;

or $R^A$ is $C\equiv CR^{35}$, wherein $R^{35}$ is hydrogen, lower alkyl of up to 3 C-atoms, aryl of up to 12 C atoms, or $CHR^{33}R^{30}$, wherein $R^{33}$ is as defined above and $R^{30}$ is halogen, $OR^{40}$ or $NR^{41}R^{42}$, wherein $R^{40}$ is hydrogen, lower alkyl of up to 3 C-atoms, or $C_4$ or 5-alkylene thereby forming a 5- or 6-membered heterocyclic ring containing O and wherein $R^{41}$ and $R^{42}$ are the same or different and each is hydrogen or lower alkyl, or together are $C_4$ or 5-alkylene forming a ring with the N-atom, or $R^{35}$ is

wherein $R^{23}$ and $R^{24}$ are as defined above;

or $R^A$ is $SO_2R^2$, wherein $R^2$ is alkyl of up to 6 C atoms;

and wherein each compound may contain 1–4 identical or different non-H $R^A$ groups; and (3) those compounds wherein $R^A$ is as defined above originally;

Z is as defined in (2) above, and $R^C$ is alkoxyalkyl of up to 6 C-atoms, or $(CH_2)_nOR^{20}$ wherein $R^{20}$ is alkyl of up to 6 C-atoms, cycloalkyl of 3–6 C-atoms or aralkyl of up to 8 C-atoms and n is an integer of 1 to 3.

The compounds of this invention have valuable pharmacological properties. In particular they exert effects on the central nervous system and, therefore, are suited as psychopharmaceuticals in human medicine.

DETAILED DISCUSSION

Unless indicated otherwise, within the scope of the present invention, the terms alkyl, cycloalkyl, aryl or aralkyl or their oxa-type analogs mean straight chain and branched groups with up to 10 C-atoms. Again, unless indicated otherwise herein, the terms lower alkyl, lower cycloalkyl, lower alkoxy and lower cycloalkoxy mean straight chain and branched groups with up to 6 C-atoms. Generally, equivalents of the alkyl, alkylene and cycloalkyl portions of all groups discussed above include unsaturated counterparts such as alkenyl or alkenylene or alkynyl or alkynylene with the same upper limit on the number of C-atoms. Such equivalents also include the corresponding groups wherein a C-atom is replaced by an oxa atom.

Illustratively included are methyl, ethyl, n-propyl, i-propyl, n-butyl, n-pentyl, i-butyl, benzyl, tert-butyl, cyclobutyl, cyclopentyl and their oxa-analogs.

In general, "lower" refers to 1–6 carbon atoms, unless indicated otherwise herein, e.g., as 1–3 carbon atoms. "Halogen" generally includes F, Cl, Br and I. Further, generally, various heterocyclic embodiments in this invention, e.g., for the groups $OR^{40}$, $NR^{41}R^{42}$, $CONR^6R^7$ and Y/Z, can be saturated or unsaturated. Moreover, generally, for the acids included in this invention, conventional, pharmaceutically acceptable salts with bases are equivalents and, for the bases, conventional pharmaceutically acceptable acid addition salts are equivalents.

In general, the number of substituents on the $R^{16}$ and/or $R^{17}$ groups is 1–18.

In general, the heterocyclic moieties in the compounds of this invention include, as appropriate the pyrrolyl, pyrrolidinyl, piperidinyl, hexamethylenimino, heptamethylenimino, morpholyl, thiomorpholyl, piperazinyl, tetrazolyl, 1.2.3-triazolyl, 1.2.4-triazolyl, imidazolyl, imidazolidinyl, pyrazolyl, pyrazolidinyl, isoxazolyl, oxazolyl, oxazolidinyl, thiazolyl, thiazolidinyl, 1.2.4-oxadiazolyl and 1.2.4-oxadiazolidinyl rest.

The substituents on the A ring can be in the 5,6,7 or 8 positions. Preferably, the A ring is monosubstituted or disubstituted with the non-H substituents $R^4$. The 5 and 6 positions are preferred. Monosubstitution is most preferred, e.g., in the 6-position.

When compared to known compounds, the compounds of this invention show surprisingly superior psychotropic properties. This can be demonstrated by fully conventional pharmacological protocols.

For example, it is known that certain locations in the central nervous system of vertebrates have a high specific affinity for bonding 1,4 and 1,5-benzodiazepines. (See, e.g., R. F. Squires & C. Braestrup, Nature [London] 266 [1977], 734, which is incorporated by reference herein). These locations are called benzodiazepine receptors. The pharmacological properties of the compounds of this invention can be demonstrated by determining their capacity to displace radioactively labelled flunitrazepam from such benzodiazepine receptors.

This displacement activity of the compounds of this invention has been determined by measuring $IC_{50}$ and $ED_{50}$ values. The $IC_{50}$ value is the concentration which causes a 50% displacement of the specific binding of $^3$H-flunitrazepam (1.0 nM, 0° C.) in samples with a total volume of 0.55 ml of a suspension of brain membrane, e.g., from rats.

The displacement test is carried out as follows:

0.5 ml of a suspension of untreated rat forebrain in 25 mM $KH_2PO_4$, at a pH of 7.1 (5–10 mg of tissue per sample) were incubated with $^3$H-diazepam (specific activity 14.4 Ci/millimole, 1.9 nM) or $^3$H-flunitrazepam (specific activity 87 Ci/millimole, 1.0 nM) for 40–60 minutes at 0° C. After incubation, the suspension is filtered through a glass frit, the residue is washed twice with a cold buffer solution and the radioactivity is measured by scintillation counting.

The test is then repeated, except prior to addition of the radioactively marked benzodiazepine, a given amount or an excess amount of the compound whose displacement activity is to be ascertained, is added. The $IC_{50}$ value can then be computed from the test results obtained. See Table 1, for example.

The $ED_{50}$ value represents the dosage of a test substance causing a reduction of the specific binding of the flunitrazepam to the benzodiazepine receptor in a living brain to 50% of the control value. Such an in-vivo test is carried out as follows.

The test substance is ordinarily injected subcutaneously in different doses to a group of mice. Fifteen minutes later, the $^3$H-flunitrazepam is administered intravenously. After another twenty minutes, the mice are killed. Their borebrain membranes are removed and the radioactivity of these forebrain membranes is measured by scintillation counting. The $ED_{50}$ value is determined from dose/effectiveness curves. The test results are shown in Table 1.

The compounds of the invention have an antiaggressive effect on mice. Aggression inhibition was determined on male mice (NMR from Moellegard, Denmark) with weights of 20–22 g. The mice are kept isolated for three weeks in plastic cages and when two mice are subsequently put into the same cage, they will spontaneously and almost instantaneously start to fight. This aggression is effectively inhibited by a number of psycho-pharmaceutical substances, including benzodiazepines (Valcelli, Mod. Probl. Pharmapsych. 1979, 14, 143–156).

The compounds of this invention inhibited aggression totally in a test described by Buus Lasse, Europ. J. Pharmacol., 1978, 47, 45–49. The compounds of this invention were administered subcutaneously and orally and the anti-aggressive effect half an hour later was determined. The $ED_{50}$ values were determined from the test results. These test results are listed in Table 2 for compounds of this invention and also for several known tranquilizers.

Moreover, the antagonism of pentazole-induced convulsions was investigated. The results are shown in Table II.

The test has been performed according to known test models in pharmacology, e.g., described in R. A. Turner, Screening Methods in Pharmacology, Academic Press, N.Y. and London 1965, esp. p. 164 ff., or, Woodbury, P. M., Perry, I. K. and Schmidt, R. P. Antiepileptic Drugs, Raven Press, N.Y. 1972.

TABLE I

[Structure: tricyclic ring system with rings A, B, C; $R^A$ on ring A, $R^C$ on ring C, NH on ring B, and a =C(Y)Z substituent on ring C]

| —C(Y)Z | $R^A$ | $R^C$ | (Affinity for the benzodiazepine receptor (inhibition of 3H—flunitrazepam binding)) In vitro IC$_{50}$, ng/ml | In vivo ED$_{50}$, mg/kg |
|---|---|---|---|---|
| —CHO | H | H | 30.2 | >250 |
| —COCH$_3$ | H | H | 22.4 | 100 |
| —CH=NOH | H | H | 8.7 | 19 |
| —C(=NOH)CH$_3$ | H | H | >100 | 186 |
| —CH=NNHCONH$_2$ | H | H | >100 | >250 |
| —COCH$_2$CH$_2$CH$_3$ | H | H | 20.0 | 144 |
| —C(=NOH)CH$_2$CH$_2$CH$_2$CH$_3$ | H | H | 468 | >250 |
| —CH=NOCOCH$_3$ | H | H | 169 | >250 |
| —COC$_6$H$_5$ | H | H | 4.27 | 223 |
| —CH=CHCOOC$_2$H$_5$ | H | H | 58.9 | >250 |
| —CH=NOCH$_2$C$_6$H$_5$ | H | H | 52.5 | >250 |
| —CN=N—N(CH$_3$)$_2$ | H | H | 41.7 | 54 |
| —CH=N—OCH$_3$ | H | H | 51.3 | 16 |
| —CH=N—NHCH$_3$ | H | H | 149 | 92 |
| —COCH$_2$COOC$_2$H$_5$ | H | H | 33.9 | >250 |
| —CH=N—NHC$_6$H$_5$ | H | H |  | >250 |
| —CH$_2$COOC$_2$H$_5$ | H | H | 363 | >250 |
| —CON=CHN(CH$_3$)$_2$ | H | H | 90 | >250 |
| —C(=N—NH)(N=CH) (triazole) | H | H | 104 | 26 |
| —CON=CHNHOH | H | H | 280 | 93 |
| —CON=CHNH(OCH$_3$) | H | H | 100 | >250 |
| —C(=N—N—CH$_3$)(N=CH) | H | H | >400 | 145 |
| —CONHCHO | H | H | 34 | 197 |

TABLE I-continued

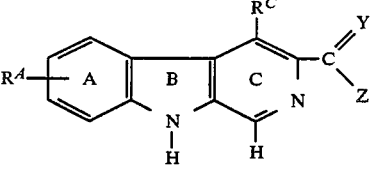

| $-C\begin{smallmatrix}Y\\\\Z\end{smallmatrix}$ | $R^A$ | $R^C$ | (Affinity for the benzodiazepine receptor (inhibition of 3H—flunitrazepam binding)  In vitro IC$_{50}$, ng/ml | In vivo ED$_{50}$, mg/kg |
|---|---|---|---|---|
| triazole with N-CH$_3$ and C-CH$_3$ | H | H | 179 | >300 |
| triazole with NH-N and C-CH$_3$ | H | H | 96 | 139 |
| oxazole with O-N and C-CH$_3$ | H | H | 0.56 | (15) |
| pyrazolinone with N=NH, CH$_2$-C=O | H | H | >100 | >250 |
| pyrazolinone with N=N-CH$_3$, CH$_2$-C=O | H | H | >400 | >250 |
| -CH=N-N(C$_2$H$_5$)$_2$ | H | H | >100 | 72 |
| isoxazolinone with N=O, CH$_2$-C=O | H | H | 156 | 100 |
| -C(CH$_3$)=N-N(CH$_3$)$_2$ | H | H | >100 | 119 |
| -CH=N-N(imidazole) | H | H | >100 | >250 |
| -CH=N-N(piperidine) | H | H | >100 | >250 |
| -CH=N-N(morpholine) | H | H | >100 | >250 |

TABLE I-continued

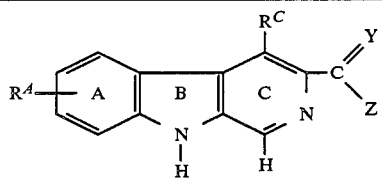

| -C(=Y)Z | $R^A$ | $R^C$ | (Affinity for the benzodiazepine receptor (inhibition of 3H—flunitrazepam binding)) In vitro IC$_{50}$, ng/ml | In vivo ED$_{50}$, mg/kg |
|---|---|---|---|---|
| —CH=N—N(piperazine)NCH$_3$ | H | H | 100 | 210 |
| —COCH$_2$CONHCH$_3$ | H | H | >100 | >250 |
| —CHO | 6-SO$_2$N(CH$_3$)$_2$ | H | >100 | >300 |
| —CH=N—N(pyrrolidine) | H | H | >100 | 49 |
| —CH=N—N(CH$_3$)$_2$ | 6-SO$_2$N(CH$_3$)$_2$ | H | 4 | 35 |
| —CH=N—N(pyrrolidine) | 6-SO$_2$N(CH$_3$)$_2$ | H | 8 | 210 |
| —CH=NOH | 6-SO$_2$N(CH$_3$)$_2$ | H | 1.7 | 300 |

TABLE II

Test Substance

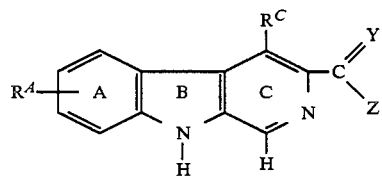

| -C(=Y)Z | $R^A$ | $R^C$ | Inhibition of Aggression ED$_{50}$, s.c. mg/kg | ED$_{50}$, p.o. mg/kg | Antagonism of pentazole-induced convulsions, ED$_{50}$ s.c., mg/kg CONVULSIONS Clonic | Tonic | DEATH |
|---|---|---|---|---|---|---|---|
| CHO | H | H | 8 | | | | |
| —COCH$_3$ | H | H | 35 | | >100 | 100 | 75 |
| —CH=CHCOOC$_2$H$_5$ | H | H | 4 | | >100 | 100 | 35 |
| —C(=NOH)CH$_3$ | H | H | | 75 | | | |

TABLE II-continued

Test Substance

[Structure: indole-fused tricyclic system with rings A, B, C; $R^A$ on ring A, $R^C$ on ring C, and $-C(=Y)Z$ substituent]

| $-C\begin{smallmatrix}Y\\\\Z\end{smallmatrix}$ | $R^A$ | $R^C$ | Inhibition of Aggression | | Antagonism of pentazole-induced convulsions, $ED_{50}$ s.c., mg/kg CONVULSIONS | | |
|---|---|---|---|---|---|---|---|
| | | | $ED_{50}$, s.c. mg/kg | $ED_{50}$, p.o. mg/kg | Clonic | Tonic | DEATH |
| $-CH=N-N(CH_3)_2$ | H | H | 7.5 | ≦50 | 20 | <10 | <10 |
| $-CH=N-OCH_3$ | H | H | 15 | | | | |
| $-CH_2COOC_2H_5$ | H | H | 75 | | | | |
| $-CH=N-N(C_2H_5)_2$ | H | H | | | >100 | 100 | 100 |
| $-C(CH_3)=N-N(CH_3)_2$ | H | H | | | >100 | 75 | 75 |
| $-CH=N-N$(piperidino) | H | H | | | >100 | 50 | >100 |
| $-CH=N-N$(morpholino) | H | H | | | 100 | 50 | 50 |
| $-CH=N-N$(pyrrolidino) | H | H | | | 20 | 15 | 15 |
| $-CH=N-N(CH_3)_2$ | 6-$SO_2N(CH_3)_2$ | H | | | 20 | 15 | 15 |
| $-CH=N-N$(pyrrolidino) | 6-$SO_2N(CH_3)_2$ | H | | | 50 | 20 | 20 |

Chlordiazepoxide ("LIBRIUM" ®)
Diazepam ("STESOLID" ®)

It can be seen from the data that the compounds of this invention effectively inhibit aggression and effectively displace flunitrazepam from benzodiazepine receptors. They are, thus, very useful as tranquilizers, non-sedating anticonvulsants, antiaggressives and anxiolytics or for stress protection. As such, they can be used for treatment of the following illustrative indications: anxiety and tension conditions, with and without depressions; unrest; disturbances resulting from stress situations or an excess of stimulation, as well as pathological aggressiveness.

The compounds of this invention can be prepared by fully conventional methods, for instance by
1. Oxidizing a compound of formula II

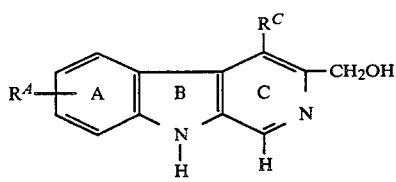

(II)

wherein
$R^A$ and $R^C$ are defined in formula I, or by reducing a compound of formula III

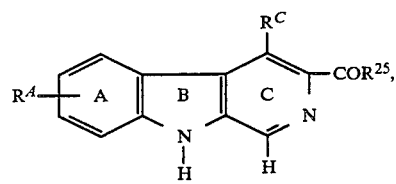

(III)

wherein $R^{25}$ is hydroxy or lower alkoxy or $NR^{26}R^{27}$, $R^{26}$ and $R^{27}$ are independently either lower alkyl or aryl and $R^A$ and $R^C$ are as defined above, while forming the corresponding aldehyde of formula IV

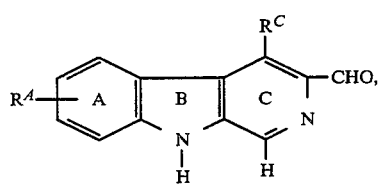

(IV)

where
$R^A$ and $R^C$ are as defined above, and optionally reacting the compound of formula IV so obtained with
(a) a compound of the formula $H_2NOR^1$, wherein $R^1$ is as defined above, whereby a compound of formula I is formed wherein Y is $NOR^1$, Z is H and $R^A$ and $R^C$ are as defined above,
(b) a compound of the formula $H_2NNR^4R^5$ wherein $R^4$ and $R^5$ are as defined above and a compound of formula I is formed, wherein Y is $NNR^4R^5$, Z is H and $R^A$ and $R^C$ are as defined above, or
(c) malonic acid or a malonic acid ester while forming a compound of the formula I wherein Y is $CHCOOR^3$, wherein $R^3$ is as defined above, Z is H and $R^A$ and $R^C$ also are as defined above;

2. Reacting a compound of formula III, wherein $R^2$ is lower alkyl or $NR^{26}R^{27}$, $R^{26}$ and $R^{27}$ being as defined above, with a compound of the formula ZMgHal, wherein Z is as defined above and Hal is a halogen atom, thereby forming a compound of formula I, wherein Y is O and $R^A$ and $R^C$ are as defined above, and optionally reacting the compound so obtained with $H_2NOR^1$ wherein $R^1$ is as defined above, or with a compound of the formula $H_2NNR^4R^5$ wherein $R^4$ and $R^5$ are as defined above while forming a compound of formula I wherein Y is $NOR^1$ or $NNR^4R^5$ and $R^A$ and $R^C$ are as defined above;

3. Reacting a compound of formula V

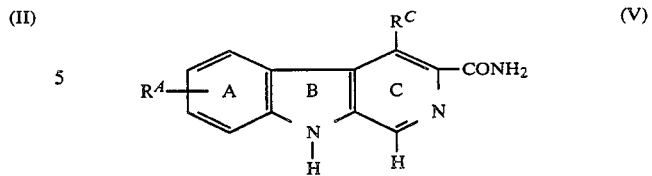

(V)

wherein
$R^A$ and $R^C$ are as defined above, with a compound of the formula $R^{21}C(OR^2)_2N(CH_3)_2$ wherein $R^{21}$ is H or lower alkyl and $R^2$ is lower alkyl, with formation of a compound of formula I wherein Y is O, Z is $N=CR^{21}N(CH_3)_2$ and optionally reacting the compound so obtained with a guanidine of formula $H_2NOR^{21}$ wherein $R^{21}$ is hydrogen or lower alkyl, or with a compound of formula $H_2NNHR^{21}$ wherein $R^{21}$ is H or lower alkyl with formation of a compound of formula I wherein Y and Z together with the adjoining C-atom for a 5-membered heterocyclic ring, and wherein $R^A$ and $R^C$ are as defined above;

4. Reacting a reactive derivative of a compound of Formula VI

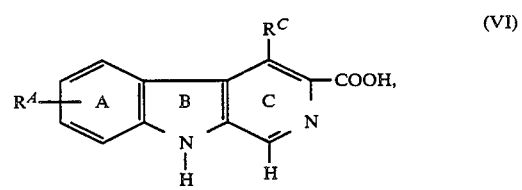

(VI)

wherein
$R^A$ and $R^C$ are as defined above, with the reaction product of (a) a monoalkylmalonate of the formula $HOOC—CH_2—COOR^=$, wherein $R^{32}$ is lower alkyl, and (b) a strong base, with formation of a compound of formula VII

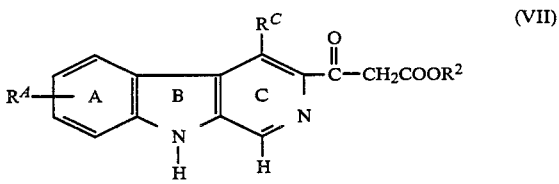

(VII)

wherein
$R^2$, $R^A$ and $R^C$ are as defined above, and reacting the compound so obtained with a hydroxylamine of the formula $H_2NNHR^{31}$ where $R^{31}$ is H or lower alkyl, urea or a urea derivative such as thiourea, guanidine or N-alkylurea, with formation of a compound of formula I
wherein Y and Z together with the adjoining C-atom form a 5 or 6-membered heterocyclic ring and wherein $R^A$ and $R^C$ are as defined above;

5. Reacting a beta-carboline-3-carbonitrile of formula VIII

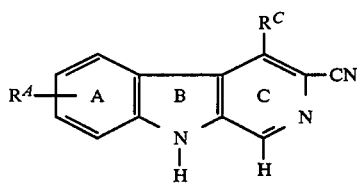

(VIII)

wherein

R$^A$ and R$^C$ are as defined above, with HN$_3$ with formation of a compound of formula I where Y and Z together with the adjoining C-atom form a tetrazole ring;

6. Cyclization of an indole derivative of formula IX,

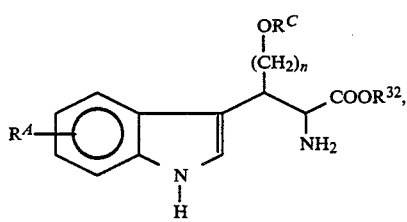

(IX)

wherein

R$^C$ is defined as in formula I;

R$^{32}$ is alkoxy of up to 6C-atoms; and

R$^A$ is CHR$^{33}$-OR$^{39}$ wherein R$^{33}$ and R$^{39}$ are the same or different and wherein R$^{33}$ is hydrogen, lower alkyl of up to 3 C-atoms or

or R$^A$ is OR$^{18}$, wherein R$^{18}$ is alkyl of up to 6 C-atoms, aryl or a straight chain or branched aralkyl of up to 12-C atoms, F, Cl, Br, I, NO$_2$, NH$_2$, CH$_3$, CF$_3$ and SCH$_3$ and SO$_2$N(CH$_3$)$_2$, with formaldehyde, and thereupon dehydrogenating the intermediarily obtained 1,2,3,4-tetrahydrocarboline and optionally (a) sulfonating and reacting the sulfonic acid so obtained with an amine of the formula NHR$^{21}$R$^{22}$ wherein R$^{21}$ and R$^{22}$ in each case independently are hydrogen or lower alkyl of up to 6 C-atoms, to form alkylaminosulfonic acid, or (b) halogenating and reacting the halogenation product so obtained to form a nitrile, or (c) nitrating and reducing the nitro compound so obtained to an amino compound, or (d) etherifying in the 4-position, or (e) esterifying in the 3-position;

7. Reacting a beta-carboline-3-carboxylic-acid alkylester of formula X

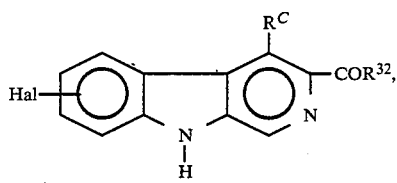

(X)

wherein

R$^C$ is as defined for formula I,

R$^{32}$ is alkoxy of up to 6C-atoms,

Hal represents bromine or iodine, with a dialkyl-phosphite of the formula

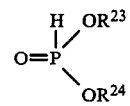

wherein R$^{23}$ and R$^{24}$ are the same or different and each is hydrogen or lower alkyl of up to 3 C-atoms, thereby forming a compound of formula I wherein R$^A$ is

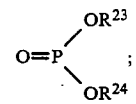

8. Reacting a beta-carboline-3-carboxylic-acid alkylester of formula X with an R$^{28}$-substituted acetylene wherein R$^{28}$ is hydrogen, lower alkyl of up to 3C-atoms, aryl of up to 12 C-atoms or methylene tetrahydropyranyl, and, when R$^{28}$ is methylene tetrahydropyranyl, treating with diluted mineral acid and oxidizing the resultant free 3-hydroxy-1-propinyl compound to a 3-oxo-1-propinyl compound or chlorinating it with thionyl chloride to form a 3-chloro-1-propinyl compound and, optionally, reacting the 3-chloro-1-propinyl compound thus obtained with a trialkyl phosphite of the formula POR$^{23}$(OR$^{24}$)$_2$, wherein R$^{23}$ and R$^{24}$ are as defined above, to obtain the corresponding 3-dialkoxyphosphoryl-1-propinyl compound, or with piperidine in the presence of a strong base to obtain the corresponding 3-piperidine-1-propinyl compound;

9. Reacting a compound of formula XI

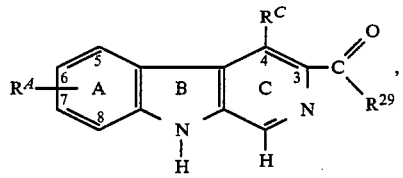

(XI)

wherein R$^{29}$ is lower alkyloxy of up to 3C-atoms and R$^C$ is as defined above, with an alkyl, alkenyl or alkynyl halide of the formula R$^{16}$(R$^{17}$)Hal, wherein Hal is chlorine, bromine or iodine, and wherein R$^{16}$ and R$^{17}$ individually are the same or different, and are hydrogen, alkyl, alkenyl or alkynyl of up to 6C-atoms, aralkyl and cycloalkyl of up to 10 C-atoms which may be substituted with halogen, hydroxy, SH, SR$^{23}$, COOR$^{23}$, nitrilo, CONR$^{23}$R$^{24}$, CHOR$^{23}$OR$^{24}$ and CHSR$^{23}$SR$^{24}$, wherein R$^{23}$ and R$^{24}$ are the same or different and are hydrogen or lower alkyl of up to 3 C-atoms, and wherein R$^{16}$ and R$^{17}$ together may form a saturated or unsaturated 3–7 membered heterocyclic ring optionally substituted with a lower alkyl of up to 3 C-atoms, S, O, OR$^{23}$, SR$^{23}$ and NR$^{23}$R$^{24}$, in which ring one C-atom may be replaced by S, O or NR$^{23}$, with formation of a compound of formula I wherein R$^A$ is NR$^{16}$R$^{17}$.

The cyclization of the compounds of formula XI in method 6 is performed in a known manner. The raw material is dissolved in an inert, water-immiscible solvent such as benzene, tolene, xylene, chlorobenzene, anisole, mesitylene and is heated with paraformaldehyde. In this manner, a derivative of 1,2,3,4-tetrahydro-9H-pyrido[3,4-b]-indole is formed, which, then, without further processing is dehydrogenated.

The dehydrogenation of the compounds obtained from the cyclization is also carried out by known procedures. One procedure is to dissolve or suspend the raw material in an inert solvent. Suitable solvents include aprotic solvents whose boiling points exceed 100° C. and which are inert with respect to the raw material. Among these for instance are included xylene, mesitylene, anisole, toluene, chlorobenzene, and diphenylether. Thereupon, elementary sulfur is added in an amount such that a molar equivalent of sulfur is used per double bond. A slight excess is unobjectionable, and in fact desirable. The reaction mixture is boiled several hours at the reflux, the reaction progress being monitored by thin film chromatography.

Another procedure is to dehydrogenate using DDQ (dichlorodicyanobenzoquinone) or chloroanile in benzene, toluene, xylene, dioxane, tetrahydrofuran, methylene chloride or dimethoxyethane at temperatures of 0° to 60° C. and for reaction times of 0.5 to 4 hours.

Another procedure is to dehydrogenate using noble metal catalysts such as platinum in finely distributed form, palladium black or palladium dust in xylene, mesitylene or cumol at 120° to 180° C. and reaction times of 2–16 h.

The preparation of sulfonic acid(s) derivatives is carried out in known manner. The raw material is dissolved in an inert solvent such as methylene chloride, chloroform and chlorosulfonic acid is added while the mixture is being cooled.

In order to prepare the corresponding alkylamine sulfonic-acid derivatives, the product previously obtained is reacted with an alkylamine.

Halogenation also is carried out by known procedures. The raw material is dissolved in an inert solvent and reacted with the corresponding halogen, for instance chlorine or bromine, possibly in the presence of a basic catalyst, at temperatures less than room temperature. Examples of inert solvents include chlorinated hydrocarbons such as methylene chloride, chloroform, dichloroethylene, etc. Suitable basic catalysts include pyridine and substituted pyridines such as dimethylaminopyridine. A basic catalyst is not essential for the chlorination.

When iodine is introduced, appropriately, not only elementary iodine but also a mixture of iodine and iodine chloride can be used, the reaction being carried out at room temperature in the presence of a basic catalyst such as pyridine.

Nitration also is carried out by known procedures. In this case, the raw material is reacted below room temperature with concentrated nitric acid. Concentrated nitric acid implies the commercial form, which may, however, be enriched with so-called fuming nitric acid. In the nitration, the acid acts both as reagent and solvent.

The optional ensuing reduction of the nitro compound so obtained into the corresponding amino compound also is carried out by known procedures.

A preferred procedure is the reduction with hydrogen in the presence of such metal catalysts as Raney nickel, platinum in finely distributed form or palladium on a suitable support such as carbon or lime at standard pressure and room temperature. However, it is also possible to make use of nascent state hydrogen, for instance using zinc/hydrochloric acid.

Etherification, if desired, of the 4-alkoxy alkyl group in the compounds of formula I also takes place by known procedures. The raw material is dissolved in, a polar solvent such as acetonitrile, dimethylformamide or 1-methyl-2-pyrrolidone and is reacted with sodium iodide and trimethylchlorosilane above room temperature.

The 4-iodoalkyl compound so obtained is again subjected by procedures known per se to a nucleophilic exchange. To this end, the raw material together with the corresponding alkali- or tetra-alkyl-ammonium-alcoholate, such as sodium ethylate or potassium ethylate, and possibly with addition of a crown ether such as 18-crown-6, dicyclohexyl-18-crown-6, dibenzo-18-crown-6-, in an inert solvent such as tetrahydrofuran, dioxane, methanol, ethanol, etc., are heated, preferably up to the boiling point of the reaction mixture.

Any desired esterification of an ester group into the 3-position also is carried out by known procedures. The raw material is reacted with an ROH alcohol in the presence of catalytic amounts of RONa for 3–6 hours at temperatures between 80° and 120° C. Where necesary, the esterification using the ROH alcohol can also be performed in the presence of an acid catalyst such as paratoluene sulfonic acid, HCl or $CuCl_2$.

To prepare the compounds of formula I following method 7, corresponding beta-carboline-3-carboxylic-acid alkylesters of formula I substituted with a halogen, in particular with chlorine, bromine and iodine in the A ring, are phosphorylated by procedures known per se.

The raw material is dissolved in an aprotic solvent such as dimethylformamide, dimethylacetamide, N-methylpyrrolidone or hexamethylphosphorictriamide. This is reacted, in the presence of a complex noble metal catalyst of the triarylphosphine class such as palladium-tetrakris-triphenylphosphine, and a strong organic base such as triethylamine, pyridine or dimethylaminopyridine, with a dialkyl phosphite such as dimethyl-, diethyl- or dipropyl-phosphite at higher temperature, that is in the range of 50°–140° C.

Again, the beta-carboline-3-carboxylic-acid alkylesters substituted with halogen in the A ring are used to prepare the compounds of formula I per method 8. The raw material is dissolved by or suspended in an aprotic solvent such as N-methyl-2-pyrrolidone or hexamethylphosphoro-triamide and is alkynylated in the presence of a base such as di- or trialkylamine, for instance diethylamine, methylethylamine, triethylamine and trimethylamine, and in the presence of a complex noble metal catalyst, such as palladium-bis-(tri-o-tolylphosphine)-dichloride or palladium-bis-(triphenylphosphine)-dichloride or a mixture of triphenylphosphine and palladous acetate and an $R^{35}$ substituted acetylene above room temperature, preferably at 40°–150° C. Suitably, the addition of cuprous salts such as cuprous iodide, can be included. Appropriately, the entire reaction is carried out while excluding air and water.

Where $R^{35}$ represents the methylenetetrahydropyranyl grouping, the compound of formula I so obtained can be hydrolyzed with a diluted mineral acid such as sulfuric, hydrochloric or perchloric acid above room temperature, the corresponding hydroxy compound, i.e. the propargyl, compound then being obtained.

The propargyl compound thus prepared, if desired, can be oxidized into the aldehyde or into the 3-oxo-1-propynyl compound. Suitable oxidizers for instance include manganese dioxide or chromic acid while using a suitable solvent. When oxidizing with manganese dioxide, all halogenated hydrocarbons such as chloroform or methylene chloride and ketones such as acetone or methylisobutylketone and also pyridine and their mixtures can be used per se. The oxidation using pyridinium dichromate is carried out in halogenated hydrocarbons or possibly in N-methyl-2-pyrrolidone.

Acetic acid is further added when the oxidation is by means of chromic acid.

The previously obtained propargyl compound, however, can be chlorinated with thionyl chloride at room temperature, a solvent not being required per se because the thionyl chloride itself acts as a solvent. The 3-chloro-1-propynyl compound thus obtained, optionally, thereupon can be reacted with a trialkylphosphite into the corresponding 3-dialkyloxyphosphoryl-1-propynyl compound by the above described method.

The previously obtained 3-chloro-1-propynyl compound, however, if desired can be reacted with piperidine in the presence of a strong base above room temperature into a corresponding 3-piperidine-1-propynyl compound. Illustrative strong bases include 1,5-diazabicyclo[5.4.0]undec-5-ene, ethyldiisopropylamine, diazabicyclononene, diazabicyclooctane, potassium tert-butylate, potassium carbonate, pulverulent potassium hydroxide, etc.

To prepare the compounds of formula I by method 9, corresponding beta-carboline-3-carboxylic acid-alkyl-esters substituted with an amino group in the A ring are reacted, by procedures known per se in a suitable solvent in the presence of a base, with a halide, tosylate or mesylate of an alkyl, alkenyl or alkynyl group, between room temperature and the boiling point of the reaction mixture.

All solvents, whether protonic or aprotic, are suitable as long as they are inert with respect to the reagents. Illustrative are aliphatic alcohols such as methanol, ethanol and propanol, ketones such as acetone and methylisobutylketone, ethers such as glycoldimethylether and diethylether, cyclic ethers such as tetrahydrofuran and dioxane, and solvents such as dimethylformamide, dimethylacetamide and N-methylpyrrolidone.

Suitable bases include all strong organic bases such as triethylamine, dimethylaminopyridine, ethylenediisopropylamine, diazabicyclo-undecene, nonene and octene. It is also possible to use alkali metal carbonates such as sodium or potassium carbonate, and, furthermore, alcoholates such as potassium tert-butylate. The alkyl, alkynyl or alkenyl halides may be substituted where appropriate, depending on the definitions of $R^5$ and $R^6$. It is important in the ring-closed compounds that a non-geminal dihalo-alkane or alkene is involved. Appropriate halogens include chlorine, bromine or iodine, and when chlorine is involved, the addition of a cuprous halide such as cuprous iodide is appropriate.

The recovery of the compounds so prepared is carried out by procedures known per se such as extraction, crystallization, chromatography, etc.

The starting materials used in method 1, for instance the 3-hydroxy-methyl-beta-carboline, can be produced by reducing the corresponding beta-carboline-3-carboxylic-acid ester with lithium aluminum hydride.

The starting materials used in methods 2 through 5 can be prepared in the manner described for instance in Canadian Patent 786,351. Similarly, all other starting materials are fully conventionally preparable.

A preferred method for preparing the starting materials includes condensing a substituted or nonsubstituted tryptophane or trypotophane ester with formaldehyde at elevated temperature with formation of a tetrahydro-beta-carboline-3-carboxylic-acid ester. The reaction of a tryptophane ester with formaldehyde preferably is carried out in a non-aqueous medium, for instance toluene. The water formed is removed by evaporation. The formyltryptophane ester is reacted with phosphoroxide chloride or polyphosphoric acid, a 3,4-dihydro-beta-carboline-carboxy ester being formed. This disproportionates into the corresponding tetrahydrocarboline and the beta-carboline aromatized in the C ring. The beta-carboline-3-carboxy-acid-ester so obtained can be hydrolyzed into the corresponding acid which thereupon is reacted with an amine into the corresponding amide and can be converted by known procedures into the corresponding nitrile.

The compounds of this invention can be used to formulate pharmaceutical preparations for instance for oral or parenteral application in mammals, including humans, in a manner known per se in galenic pharmacy.

Suitable adjuvants for formulating pharmaceutical preparations include those physiologically compatible organic and inorganic excipients for enteral and parenteral use which are inert with respect to the compounds of this invention.

Illustrative excipients, for instance, include water, salt solutions, alcohols, polyethylene glycols, polyhydroxyethoxylated ricinus oil, gelatin lactose, amylose, magnesium stearate, talc, silica gel, fatty-acid mono- and diglycerides, pentaerythritol fatty-acid ester, hydroxymethyl cellulose and polyvinyl pyrrolidone.

The pharmaceutical preparations can be sterilized and/or mixed with conventional accessory substances such as lubricants, preservatives, stabilizers, wetting agents, emulsifiers, buffers and dyes.

Injection solutions or suspensions are particularly suitable for parenteral use, especially aqueous solutions of the active compounds in polyhydroxy-ethoxylated ricinus oil.

Tablets, dragees or pills with talc and/or a hydrocarbon excipient or binder such as lactose, corn starch or potato starch are especially suited for oral application. The application may also be in liquid form, for instance as a juice, possibly sweetened.

The compounds of this invention are generally formulated in unit doses of 0.05 to 10 mg of active substance with a physiologically compatible excipient. The compounds of this invention are normally employed for the mentioned uses at dosages of 0.1 to 300 mg/day, preferably 1-30 mg/day. In general, their administration is analogous to that of the well known tranquilizers mentioned herein (Librium and Stesolid) taking into account conventional factors such as differential potencies.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A mixture of 3.3 g of 3-hydroxymethyl-beta-carboline, 300 ml of water-free pyridine and 9.9 g of lead tetra-acetate is heated in an oil bath for 4 h at about 80° C. After cooling and evaporation, 150 ml of water is added. The crystalline residue is filtered off, washed with a 5% aqueous potassium carbonate solution and then again with water. The air-dried product (3.5 g) is boiled in 0.7 liters of 2-propanol with activated carbon and is filtered hot. After evaporation, 2.7 g of beta-carboline-3-carboxaldehyde is obtained, with a melting point of 270° C. (decomposition).

In a similar manner, 6-dimethylsulfamoyl-beta-carboline-3-carboxaldehyde with a melting point of 172°–174° C. and 192°–195° C. (decomposition) is obtained from 6-dimethylsulfamoyl-3-hydroxymethyl-beta-carboline, and 4-ethyl-beta-carboline-3-carboxaldehyde with a melting point of 199°–205° C. is obtained from 4-ethyl-3-hydroxymethyl-beta-carboline.

EXAMPLE 2

A solution of 3.1 g of potassium hydroxide in 40 ml of methanol is added to a mixture of 150 ml of dimethyl-formamide, 6.9 g of beta-carboline-3-carboxaldehyde and 3.1 g of hydroxylamino-hydrochloride. The reaction mixture is allowed to stand at room temperature overnight. After evaporation, 50 ml of water is added. The reaction product is filtered off. 6.9 g of the air-dried product is heated in the steam bath together with 35 ml of 2 propanol and, after cooling, is filtered off. 5 g of beta-carboline-3-carboxaldehyde-oxime with a melting point of 229°–231° C. is obtained.

The following were prepared in similar manner:
beta-carboline-3-carboxaldehyde-oxime-benzylether, m.p. 157°–159° C.;
beta-carboline-3-carboxaldehyde-oxime-methylether, m.p. 215°–217° C.; and
beta-carboline-3-carboxaldehyde-semicarbazone, m.p. 252°–255° C.

EXAMPLE 3

A Grignard solution is prepared from 8 g of magnesium in 100 ml of ether and 47 g of methyl iodide in 100 ml of ether. To this solution is added a solution of 5 g of beta-carboline-3-dimethylcarboxamide in 400 ml of tetrahydrofuran. The reaction mixture is agitated for 1 h at room temperature and then is heated 2 h in the steam bath to the boiling point. Thereupon, a mixture of 10 ml of water in 20 ml of tetrahydrofuran is added and the reaction mixture is evaporated under reduced pressure. 480 ml of 2N hydrochloric acid and then 100 ml of concentrated ammonium hydroxide are added to the residue. After extractions with 300 and 100 ml of chloroform, 4.3 g of raw product are obtained. After recrystallization in 20 ml in propanol, 2.6 g of 3-acetyl-beta-carboline with a m.p. of 240°–244° C. is obtained.

The following were prepared in similar manner:
3-pentanoyl-beta-carboline, m.p. 174°–175° C. and
3-benzoyl-beta-carboline, m.p. 226°–227° C.

EXAMPLE 4

To a solution of 1.0 g of potassium hydroxide in 25 ml of methanol, there is added a mixture of 0.85 g of 3-acetyl-β-carboline, 75 ml of methanol and 1.0 g of hydroxyamino hydrochloride. The reaction mixture is allowed to stand for 4 hours at room temperature. After evaporation, water is added and then the mixture is brought to pH 7 with glacial acetic acid. The solid reaction product is filtered and washed with water and ether. 0.6 g of 3-acetyl-β-carboline-oxime with an m.p. of 250° C. (decomposition) is obtained. In analogous manner there is obtained: 3-pentanoyl-β-carboline-oxime, m.p. 95°–120° C.

EXAMPLE 5

A mixture of 1.0 g of beta-carboline-3-carboxaldehyde, 10 ml of dimethyl-formamide and 3 ml of N,N-dimethyl hydrazine is introduced into a glass autoclave. The air is replaced by nitrogen. After stirring for 3 h, the reaction mixture is allowed to stand overnight at room temperature. After adding 25 ml of water, the reaction mixture is extracted with 100 and 50 ml of chloroform. The chloroform phase is dried using magnesium sulfate, then filtered. Then, the chloroform is evaporated. After adding 10 ml of ether, the reaction product is filtered off. 0.9 g of beta-carboline-3-carboxaldehyde-dimethylhydrazone with a m.p. of 203°–206° C. is obtained.

The following were prepared in similar manner:
beta-carboline-3-carboxaldehyde-methylhydrazone, m.p. 162°–164° C.;
beta-carboline-3-carboxaldehyde-phenylhydrazone, m.p. 242°–246° C.;
beta-carboline-3-carboxaldehyde-diethylhydrazone, m.p. 133°–140° C.;
3-acetyl-beta-carboline-dimethylhydrazone, m.p. 70°–72° C.;
3-[(4-(1.2.4-triazolyl)iminomethylene]-beta-carboline, m.p. 260° C.;
3-[(N-piperidinyl)iminomethylene]-beta-carboline, m.p. 247°–249° C.;
3-[(N-morpholinyl)iminomethylene]-beta-carboline, m.p. 233°–235° C.;
3-[(4-(1-methylpiperazinyl)iminomethylene]-beta-carboline, m.p. 212°–214° C.; and
3-[(N-(pyrrolidinyl)iminomethylene]-beta-carboline, m.p. 217°–223° C.

In similar manner, except for using 1.0 g of 6-dimethylsulfamoyl-beta-carboline-3-carboxaldehyde as the raw material, the following were prepared:
6-dimethylsulfamoyl-beta-carboline-3-carboxaldehyde-dimethyl-hydrazone, m.p. 242°–249° C.; and
6-dimethylsulfamoyl-3-[(N-pyrrolidinyl)iminomethylene]-beta-carboline, m.p. 215°–226° C.

In a similar manner, 4-ethyl-beta-carboline-3-carboxaldehyde-dimethylhydrazone with a m.p. of 162°–166° C. is prepared from 4-ethyl-beta-carboline-3-carboxaldehyde.

EXAMPLE 6

A mixture of 1.0 g of beta-carboline-3-carboxamide and 3 ml of dimethyl-formamide-dimethylacetal is heated for 3 h at about 115° C. in an oil bath. After cooling, the crystals are collected on a glass frit and washed with 1 ml of dimethylformamide and then with 20 ml of ether. 1.2 g of N-[(dimethylamino)methylene]-beta-carboline-3-carboxamide with a m.p. of 307°–317° C. is obtained.

N-[(dimethylamino)ethylidene]-beta-carboline-3-carboxamide with a m.p. of 254°–257° C. is prepared similarly.

EXAMPLE 7

A mixture of 0.48 g of guanidine hydrochloride, 2.5 ml of 1N sodium hydroxide, 3.5 ml of glacial acetic acid and 1.1 g of N-[(dimethylamino)methylene]-beta-carboline-3-carboxamide is allowed to stand 2 h at room temperature. After adding 5 ml of dioxane and 5 ml of glacial acetic acid, the reaction mixture is heated at 90°

C. for one hour. After cooling, the precipitate is filtered off and washed with water. 0.6 g of beta-carboline-3-(N-formylcarboxamide) with a m.p. of 237°–241° C. is obtained.

EXAMPLE 8

A mixture of 0.35 g of hydroxylamine hydrochloride, 1.5 ml of water, 1.0 ml of 5N sodium hydroxide, 3.5 ml of acetic acid and 1.1 g of N-[(dimethylamino)methylene]-beta-carboline-3-carboxamide is allowed to stand for ½ h at room temperature. After adding 3 ml of water, the white precipitate is filtered off and washed with water. 1.0 g of N-[(hydroxyamino)methylene]-beta-carboline-carboxamide with a m.p. of 235°–240° C. is obtained.

N-[(methoxyamino)methylene]-beta-carboline-3-carboxamide with a m.p. of 220°–245° (sublimation) is prepared in similar manner.

EXAMPLE 9

A mixture of 2.0 g of beta-carboline-3-carboxaldehyde, 2.0 g of malonic acid, 40 ml of water-free pyridine and 0.1 ml of piperidine is heated in a steam bath for 4 h. The solvent is evacuated in vacuum and after adding 20 ml of 2-propanol, the precipitate is filtered off. 2.3 g of 3-(3-beta-carbolinyl)-acrylic acid with a m.p. of 240°–260° C. (decomposition) is obtained.

EXAMPLE 10

A mixture of 2.3 g of 3-(3-beta-carbolinyl)-acrylic-acid, 70 ml of 99% ethanol, and 10 ml of concentrated sulfuric acid is boiled at the reflux for 5 h. After cooling, the reaction mixture is placed in an ice mixture of 100 g of ice and 40 ml of concentrated ammonium hydroxide. The reaction mixture is filtered off. 2.2 g of ethyl-3-(3-beta-carbolinyl)-acrylate with a m.p. of 132°–134° C. is obtained.

2.2 g of 3-(3-beta-carbolinyl)-acrylic-acid-ethylester is recrystallized at higher temperature out of 5 ml of acetic acid. 1.6 g of product with a m.p. of 142°–144° C. is obtained.

EXAMPLE 11

A mixture of 1.4 g of 3-carboethoxyacetyl-beta-carboline, 30 ml of dimethyl-formamide and 4 ml of methylhydrazine is heated for 6 h in a glass autoclave at 80° C. The reaction medium is then evaporated and, after adding 10 ml of methanol, the reaction product is filtered off and washed with 10 ml of methanol. 1.0 g of 3-(3-(1-methyl-pyrazolone-5)-yl)-beta-carboline with a m.p. of 267°–270° C. (decomposition) is obtained.

In similar manner, 3-(3-pyrazolone-5)-yl)-beta-carboline with a m.p. in excess of 300° C. (decomposition) and 3-(3-(isooxazolone-5-yl)-beta-carboline, with a m.p. in excess of 350° C. (decomposition) are prepared.

EXAMPLE 12

A mixture of 1.0 g of N-[(dimethylamino)methylene]-beta-carboline-3-carboxamide, 10 ml of glacial acetic acid and 270 microliters of 80% hydrazine hydrate is heated for 2 h in an oil bath at about 90° C. After evaporation, 10 ml of ether are added. The precipitate is filtered off and washed with ether. There is obtained 0.9 g of 3-(3-(1,2,4-triazole)yl)-beta-carboline with a m.p. of 285°–290° C.

3-(3-(1-methyl-1.2.4.-triazole)-yl)-beta-carboline with a m.p. of 277°–278° C. is prepared in a similar manner.

From N-[(dimethylamino)ethylidene]-beta-carboline-3-carboxamide, there is prepared analogously 3-(3-(2,4-dimethyl-1,2,4-triazole)-yl)-β-carboline, m.p. 192°–198° C. and 3-(3-(5-methyl-1,2,4-triazole)-yl)-β-carboline, m.p. 151°, 155° C.

EXAMPLE 13

A mixture of 1.3 ml water, 1.3 ml of 4M sodium hydroxide, 7 ml of glacial acetic acid, 5 ml of dioxane, 0.35 g of hydroxylamine-hydrochloride and 1.0 g of N-[(dimethylamino)ethylidine]-beta-carboline-3-carboxamide is heated at about 90° C. for 2 h. After cooling and addition of 20 ml of water, the precipitate is filtered off and washed with 40 ml of water. 0.8 g of 3-(5-(3-methyl-1,2,4-oxadiazole)-yl)-beta-carboline with a m.p. of 314°–316° C. is obtained.

EXAMPLE 14

A mixture of 3.0 g of thionyl chloride and 50 ml of water-free tetrahydrofuran is added dropwise and while stirring into a solution of 6.9 g of imidazole in 150 ml of water-free tetrahydrofuran. After further stirring for 15 minutes, the reaction mixture is filtered off and 5.0 g of beta-carboline-3-carboxylic-acid is added to the filtrate. The reaction mixture is stirred for 18 h.

A Grignard solution is prepared from 3.6 g of magnesium, 150 ml of water-free tetrahydrofuran and 15 g of 2-bromopropane. The solution is allowed to stand overnight. The next day, this isopropyl-magnesium-bromide solution is dripped into a solution of 8 g of freshly distilled monoethylmalonate in 50 ml of tetrahydrofuran. The reaction mixture is stirred for ½ h. The two reaction mixtures thus prepared are combined dropwise and stirred for 3 h. The reaction mixture is allowed to stand overnight at room temperature and then is poured on a mixture of 200 g of ice and 20 ml of concentrated hydrochloric acid. After adding 20 g of sodium bicarbonate and 100 g of sodium chloride, the tetrahydrofuran phase is removed, dried with sodium sulfate and evaporated. The residue (4.0 g) is stirred into 400 ml of methylene chloride and filtered. After evaporating the filtrate, 2.7 g of 3-carboethoxy-acetyl-beta-carboline with a m.p. of 166°–168° C. is obtained.

EXAMPLE 15

185 mg of sodium azide and 370 mg of aniline hydrochloride are added to a solution of 500 mg of beta-carboline-3-carbonitrile in 10 ml of dimethylformamide in a glass autoclave. The autoclave is heated with stirring in an oil bath at 125° C. for 15 h. After cooling the reaction mixture, 185 mg of sodium azide is added and the reaction mixture is stirred at 155° C. for another 19 h. The solvent is removed in vacuum. The reaction product is mixed with 25 ml of water, set to a pH of 2 by means of 4N hydrochloric acid, filtered, and twice washed with 10 ml of water. 452 mg of 3-(5-tetrazolyl)-beta-carboline with a m.p. exceeding 300° C. is obtained.

EXAMPLE 16

2 ml of bromine in 20 ml of chloroform is dripped into a mixture of 1.0 g of 3-(5-(3-methyl-1,2,4-oxadiazole)-yl)-beta-carboline, 50 ml of chloroform and 3.5 ml of pyridine, with stirring, at a temperature of 0°–5° C. After stirring for 2 h at the same temperature, 50 ml of chloroform is added. The solution is then washed with a sodium thiosulfate solution and then with water. After drying by means of magnesium sulfate, the solution is evaporated until dry. The residue is recrystallized out of pyridine. 0.6 g of 6-bromo-3-(5-(3-methyl-1,2,4-oxadiazole)-yl)-beta-carboline with a m.p. of 290°–295° C. is obtained.

EXAMPLE 17

1.0 g of 3-(5-(3-methyl-1,2,4-oxadiazole)-yl)-beta-carboline is added to 20 ml of 65% nitric acid. The reaction mixture is stirred for 2 h at room temperature. After adding 100 g of ice water, the precipitate is filtered off, washed with water and dried in air. After recrystallizing out of pyridine, 0.6 g of 3-(5-(3-methyl-1,2,4-oxadiazole)-yl)-6-nitro-beta-carboline with a m.p. in excess of 330° C. (decomposition) is obtained.

EXAMPLE 18

A mixture of 0.2 g of 3-(5-(3-methyl-1,2,4-oxadiazole)-yl)-6-nitro-beta-carboline, 100 ml of 99% ethanol and 0.2 g of palladium/carbon (5%) is hydrogenated at 1 atm and room temperature. The reaction mixture is filtered and the solvent is removed by evaporation. 0.15 g of 6-amino-3-(5-(3-methyl-1,2,4-oxadiazole)-yl)-beta-carboline with a m.p. of 310°–320° C. (decomposition) is obtained.

EXAMPLE 19

20.3 g of beta-methoxymethyl-tryptophane-ethylester is dissolved in 350 ml of benzene, mixed with 2.48 g of paraformaldehyde and heated for 3.5 h in the water separator. After cooling, the benzene is distilled off, the residue is absorbed in 350 ml of toluene, and after adding 4.5 g of 10% palladium carbon, the mixture is heated with reflux for 20 h. The cooled solution is filtered and concentrated. The residue is chromatographed on silica gel with hexane/ethyl-acetate. The crystallization of the main fraction out of ethylacetate/diisopropylether yields 6.4 g of 4-methoxymethyl-beta-carboline-3-carboxylic-acid-ethylester with a m.p. 118°–119° C.

Raw-material preparation (a) 191.0 ml of isopropylamine, while being ice-cooled, is dripped for 2 h to mix with 165.3 g of methoxyacetaldehyde so that the inside temperature shall not exceed 10° C. This is followed by stirring for 30 minutes at 5° C., and by mixing with solid potassium hydroxide until there are two phases; then, the upper phase is separated and is mixed again with potassium lye and allowed to stand for 12 h at 5° C. This is followed by filtration and the filtrate is distilled over about 2 g of barium oxide in a water jet vacuum. 110.9 g of isopropylimine of the methoxyacetaldehyde, with a m.p. of 35°–39° C. (40–30 mm Hg) is obtained.

(b) 110.9 g of the previously obtained imine in 230 ml of benzene is dripped into a solution of 96.5 g of indole in 510 ml of glacial acetic acid in the presence of ice cooling in such a manner that the inside temperature does not exceed 10° C. Then stirring proceeds for 12 h at 5° C. The reaction solution thereafter is thoroughly mixed into about 1.7 liters of ice water, the organic phase is separated and the aqueous phase is extracted twice, each time with 180 ml of benzene. The aqueous phase while being ice-cooled is adjusted dropwise to a pH of 13 with 6N soda lye and extracted with benzene and ether. The extracts of the alkaline phase are dried on sodium sulfate and concentrated. 183.9 g of light-yellow oil, which can be used in the next stage without further purification, is obtained.

(c) A solution of 92.0 g of the above obtained product in 1.3 liters of toluene is mixed with 55.2 g of nitroacetic-acid-ethylester and stirred for 16 h under argon at 80° C. After cooling, the mixture is washed twice, each time with 400 ml of 1N hydrochloric acid, then with a saturated sodium chloride solution, dried on sodium sulfate and concentrated. 155.9 g of an adduct in the form of an oily isomeric mixture is obtained which is used without further processing in the secondary reaction.

(d) 24.9 g of the above obtained adduct is dissolved in 600 ml of ethanol and, after adding about 32 g of Raney nickel, is hydrogenated at room temperature and normal pressure. After absorbing 5650 ml of hydrogen, the mixture is filtered off the catalyst and concentrated. 20.3 g of beta-methoxymethyl-tryptophane-ethylester is obtained as an oily mixture of isomers.

EXAMPLE 20

The following beta-carbolines are prepared similarly to the procedure of example 19:

5-methoxy-4-methoxymethyl-beta-carboline-3-carboxylic-acid-ethylester, m.p. 168°–170° C.;

6-methoxy-4-methoxymethyl-beta-carboline-3-carboxylic-acid-ethylester, m.p. 175°–177° C.;

7-methoxy-4-methoxymethyl-beta-carboline-3-carboxylic-acid-ethylester, m.p. 161°–163° C.;

5-benzyloxy-4-methoxymethyl-beta-carboline-3-carboxylic-acid-ethylester, m.p. 185°–188° C.;

6-chloro-4-methoxymethyl-beta-carboline-3-carboxylic-acid-ethylester, m.p. 206°–208° C.;

5-fluoro-4-methoxymethyl-beta-carboline-3-carboxylic-acid-ethylester, m.p. 182°–184° C.;

6,7-dimethoxy-4-methoxymethyl-beta-carboline-3-carboxylic-acid-ethylester, m.p. 163°–164° C.; and 6,7-dichloro-4-methoxymethyl-beta-carboline-3-carboxylic-acid, m.p. 199°–203° C.

EXAMPLE 21

2.5 g of alpha-nitro-beta-(2-methoxy)-indolyl-(3)-propionethylester is hydrogenated analogously to 1(c) and reacted analogously to 1(d) with paraformladehyde and dehydrogenated with palladium black and then chromatographed. After the main fraction crystallizes out of ethyl acetate, 600 mg of 4-[2-methoxyethyl]-beta-carboline-3-carboxylic-acid-ethylester with a m.p. of 181°–183° C. is obtained.

Raw-material preparation (a) Using 16.1 ml of isopropylamine and 16.6 g of beta-methoxy-propionaldehyde (prepared per Angew. Schem. 62, 115, [1950]), and under the conditions of the example 1(a), 22.9 g of the isopropylimine of beta-methoxy-propionaldehyde is obtained as an isomeric E,Z mixture.

(b) A solution of 20.7 g of indole in 104 ml of glacial acetic acid is reacted under the conditions of example 1(b) with 22.9 g of the previously obtained imine in 54 ml of benzene. 19.2 g of the condensation product is obtained in the form of a brown oil.

(c) 19.2 g of the previously obtained product is reacted with 10.4 g of nitroacetic-acid-ethylester under the conditions of example 19(c). After chromatography using silica gel with hexane/acetic-acid, 8.5 g of alpha-nitro-beta-(2-methoxy)-indolyl-(3)-propionethylester is obtained in the form of a yellow oil.

EXAMPLE 22

Similarly to example 21, the following beta-carbolines are prepared using substituted indoles:

6,7-dimethoxy-4[2-methoxyethyl]-beta-carboline-3-carboxylic acid-ethylester, m.p. 206°-208° C.
6-methoxy-4-[2-methoxyethyl]-beta-carboline-3-carboxylic-acid-ethylester, m.p. 189°-191° C.;
6-chloro-4-[2-methoxyethyl]-beta-carboline-3-carboxylic-acid-ethylester, m.p. 232°-234° C.;
5-benzyloxy-4-[2-methoxyethyl]-beta-carboline-3-carboxylic-acid-ethylester, m.p. 174°-176° C.; and
6-benzyloxy-4-methoxymethyl-beta-carboline-3-carboxylic-acid-ethylester, m.p. 165°-166° C.

EXAMPLE 23

A solution of 300 mg of 4-methoxymethyl-beta-carboline-3-carboxylic-acid-ethylester in 15 ml of methylene chloride is mixed dropwise with ice cooling with 0.6 ml of chlorosulfonic acid. Thereupon, the mixture is stirred for 2 h at 25° C., then cooled to 5° C. and 6 ml of a 40% aqueous dimethylamino solution is dripped into it. The processing consists of dilution with acetic acid, washing with water and a saturated NaCl solution, drying on sodium sulfate and concentration. The crystallization of the raw product from ethylacetate/ethanol yields 130 mg of 6-dimethylamino-sulfonyl-4-methoxymethyl-beta-carboline-3-carboxylic-acid-ethylester with a m.p. of 191°-193° C.

EXAMPLE 24

A solution of 284 mg of 4-methoxymethyl-beta-carboline-3-carboxylic-acid-ethylester in 13 ml of chloroform is cooled to −30° C. and is dropwise mixed with 0.05 ml bromine in 1 ml of chloroform. This mixture is stirred for 2 h at −20° C. to −10° C., is poured into ice-cold 10% sodium hydrogen sulfite solution and extracted with methylene chloride. The crystallization in ethyl acetate yields 240 mg of 6-bromo-4-methoxymethyl-beta-carboline-3-carboxylic-acid-ethylester with a m.p. 207°-209° C.

EXAMPLE 25

0.5 ml of bromine in 3 ml of chloroform are dripped at room temperature into a solution of 250 mg of 4-methoxymethyl-beta-carboline-3-carboxylic-acid-ethylester and the mixture is stirred at room temperature for 2 h. After processing as in example 21 and crystallization in hexane/ethyl-acetate, 260 mg of 6,8-dibromo-4-methoxymethyl-beta-carboline-3-carboxylic-acid-ethylester with a m.p. of 98°-99° C. is obtained.

EXAMPLE 26

2.0 g of 4-methoxymethyl-beta-carboline-3-carboxylic-acid-ethylester is added batchwise in the presence of ice cooling to a mixture of 19.3 ml of 65% nitric acid and 9.65 ml of fuming nitric acid. The mixture is then stirred for 3 hours at 5° C. The reaction mixture is then dripped into ice water and made alkaline by means of a concentrated aqueous ammonia solution, and filtered. The precipitate is washed with water, dried, then suspended in 30 ml of ethyl acetate and heated for 15 minutes with reflux. After cooling, th filtration produces 1.85 g of 4-methoxy-methyl-6-nitro-beta-carboline-3-carboxylic-acid-ethylester with a m.p. of 274°-276° C.

In similar manner, the nitration of 2 g of 4-[2-methoxy-ethyl]-beta-carboline-3-carboxylic-acid-ethylester produces the corresponding nitro compound 6-nitro-4-[2-methoxyethyl]-beta-carboline-3-carboxylic-acid-ethylester in an amount of 1.80 g with a m.p. of 283°-286° C.

EXAMPLE 27

1.7 g of the two nitro derivatives obtained in example 26 are hydrogenated in 70 ml of tetrahydrofuran and 70 ml of ethanol after adding 300 mg of 10% palladium dust at room temperature and standard pressure. After the introduction of 420 ml of hydrogen, the mixture is filtered and concentrated. The crystallization in ethyl acetate yields 1.2 g of 6-amino-4-methoxymethyl-beta-carboline-3-carboxylic-acid with a m.p. of 199°-201° C. and 1.1 g of 6-amino-4-methoxymethyl-beta-carboline-3-carboxylic-acid-ethylester with a m.p. of 238°-242° C.

EXAMPLE 28

A solution of 1.0 g of 4-methoxymethyl-beta-carboline-3-carboxylic-acid-ethylester in 20 ml of methylene chloride and 1.5 ml of pyridine is mixed dropwise with 1.5 ml of iodine chloride at room temperature. After 60 minutes, another 1.5 ml of iodine chloride is added and then 200 mg of iodine. The mixture is stirred for another 2 h at room temperature and then poured into an ice-cold saturated sodium thiosulfate solution, followed by extraction with methylene chloride. Crystallization in ethyl acetate yields 520 mg of 6-iodo-4-methoxymethyl-beta-carboline-3-carboxylic-acid-ethylester with a m.p. of 204°-206° C.

EXAMPLE 29

A suspension of 300 mg of the 6-iodo-derivative prepared in example 10, 5 ml of dimethylformamide and 105 mg of copper cyanide is stirred for 2 h at 160° C. under argon. After being cooled, it is poured into an aqueous ammonia solution and extracted with methylene chloride. Crystallization in ethyl-acetate/ethanol yields 160 mg of 6-cyano-4-methoxymethyl-beta-carboline-3-carboxylic-acid-ethylester with a m.p. of 252°-255° C.

EXAMPLE 30

A suspension of 1.5 g of 4-methoxymethyl-beta-carboline-3-carboxylic-acid-ethylester, 20 ml of acetonitrile, 3.1 g of sodium iodide and 2.7 ml of trimethylchlorosilane is stirred at 60° C. for 2 h. After cooling, it is poured into ice water and extracted with ethyl acetate. The extracts are washed with saturated sodium thiosulfate solution, dried and concentrated. 1.65 g of 4-iodo-methyl-beta-carboline-3-carboxylic-acid-methylester with a m.p. of 280°-286° C. is obtained.

1.65 g of the above obtained 4-iodo-methyl derivative is added to a fresh solution of 1.5 g of sodium ethylate in 20 ml of ethanol and 20 ml of tetrahydrofuran and the mixture is heated with reflux for 2 h. After cooling it is poured into a 10% sodium dihydrogen phosphate solution and extracted with ethyl acetate. Chromatography on silica gel with hexane/acetone and crystallization of the main fraction from ethyl acetate yield 720 mg of 4-ethoxymethyl-3-carboline-3-carboxylic-acid-ethylester with a m.p. 125°-127° C.

EXAMPLE 31

30 mg of sodium is dissolved in 15 ml of absolute methanol. Then, 300 mg of 4-methoxymethyl-beta-carboline-3-carboxylic-acid-ethylester is added and the mixture is heated with reflux for 2 h. The cooled solution is poured into a sodium dihydrogen phosphate solution and extracted with ethyl acetate. Crystallization in hexane/methylene-chloride yields 270 mg of 4-methoxymethyl-beta-carboline-3-carboxylic-acid-methylester with a m.p. 134°–135° C.

EXAMPLE 32

Similarly to example 31, the compounds below are prepared from the particular beta-carboline-3-carboxylic-acid-ethylesters with the corresponding alcohols:
6,7-dimethoxy-4-methoxymethyl-3-carboline-3-carboxylic-acid-methylester, m.p. 163°–164° C.;
6,7-dimethoxy-4-methoxymethyl-beta-carboline-3-carboxylic-acid-n-propylester, m.p. 172°–174° C.;
6,7-dimethoxy-4-methoxymethyl-beta-carboline-3-carboxylic-acid-isopropylester, m.p. 166°–168° C.; and
4-methoxymethyl-beta-carboline-3-carboxylic-acid-n-propylester, m.p. 154°–157° C.

EXAMPLE 33

1.46 g of 6-iodo-beta-carboline-3-carboxylic-acid-ethylester is added anhydrously to a mixture of 608 g of diethylphosphite, 448 g of triethylamine, 240 mg of palladium tetrakristriphenylphosphine and 60 ml of N-methyl-2-pyrrolidone and is stirred for 12 h at 90° C. After concentration is an oil pump vacuum, the residue is chromatographed on 75 g of silica gel with methylene-chloride/acetone in the ratio of 1/1 as the eluant. The corresponding consolidated fractions are chromatographed on 25 g of silica gel with methylene-chloride/ethanol=10/2 as the eluant. 421 mg of 6-diethoxy-phosphoryl-beta-carboline-3-carboxylic-acid-ethylester in the form of an oil is obtained.

EXAMPLE 34

The compounds below are prepared in similar manner from the corresponding iodine compounds:
6-diisopropoxyphosphoryl-beta-carboline-3-carboxylic-acid-ethylester;
6-diethoxyphosphoryl-4-methyl-beta-carboline-3-carboxylic-acid-ethylester;
6-diethoxyphosphoryl-4-methoxymethyl-beta-carboline-3-carboxylic-acid-ethylester;
5-diethoxyphosphoryl-beta-carboline-3-carboxylic-acid-ethylester; and
6-diethoxyphosphoryl-beta-carboline-3-carboxylic-acid-methylester;
all in the form of oils.

EXAMPLE 35

347 mg of 6-bromo-4-ethyl-beta-carboline-3-carboxylic-acid-ethylester, 32 mg of palladium-bis-(tri-o-tolyl-phosphine)-dichloride, 32 mg of cuprous iodide, 5 ml of diethylamine, 5 ml of N-methyl-2-pyrrolidone and 250 mg of 3-dimethylamino-1-propine are heated anhydrously and under nitrogen for 7.5 h at 80°–90° C. After concentration in an oil pump vacuum, the residue is chromatographed on 30 g of silica gel with methylene-chloride/methanol (10/2) as the eluant. The correspondingly consolidated fractions are separated by preparative film chromatography and 170 mg of 6-(3-dimethylamino-1-propinyl)-4-ethyl-beta-carboline-3-carboxylic-acid-ethylester is obtained in the form of an oil.

EXAMPLE 36

The following compounds are prepared in similar manner:
6-(3-dimethylamino-1-propinyl)-beta-carboline-3-carboxylic-acid-ethylester, (m.p. 253°–258° C. from ethanol),
6-(3-dimethylamino-1-propinyl)-beta-carboline-3-carboxylic-acid-ethylester, (m.p. 270°–275° C.), and
5-(3-dimethylamino-1-propinyl)-beta-carboline-3-carboxylic-acid-ethylester, (m.p. 228°–229° C., decomposition).

EXAMPLE 37

1.6 g of 6-bromo-beta-carboline-3-carboxylic-acid-ethylester together with 30 ml of dimethylamine is added under nitrogen and with exclusion of water to a mixture of 70 mg of cuprous iodide, 70 mg of palladium (bis[tri-o-tolyl]-phosphine-dichloride, and 1 ml of tetrahydropyran-2-yl-propargylether in 50 ml of N-methyl-2-pyrrolidone. After 2 h at 100°–120° C., another 1 ml of tetrahydropyran-2-yl-propargylether and 70 mg of cuprous iodide and 70 mg of palladium (bis[tri-o-tolyl]-phospine)dichloride are added, and again the mixture is kept at 100°–120° C. for 3 h.

Next, the mixture is concentrated with an oil pump vacuum. The residue is triturated with ethanol and evacuated. A small sample of the crystals is recrystallized from ethanol/diisopropylether. 40 mg of 6-(3-tetrahydropyran-2-yl-oxy-1-propinyl)-beta-carboline-3-carboxylic-acid-ethylester (m.p. 265°–268° C.) is obtained. The remainder of the crystals is processed as in example 6. This remainder is still contaminated by the 6-bromine compound.

EXAMPLE 38

The following compounds are prepared in similar manner:
6-(3-methoxy-1-propinyl)-beta-carboline-3-carboxylic-acid-ethylester,
6-(2-carboethoxy-1-ethinyl)-beta-carboline-3-carboxylic-acid-ethylester, and
6-(phenylethinyl)-beta-carboline-3-carboxylic-acid-ethylester, m.p. 281°–287° C.

EXAMPLE 39

1100 mg of the mixture described in example 5 and consisting of 6-bromo-beta-carboline-3-carboxylic-acid-ethylester and 6-(3-tetrahydropyran-2-yl-oxy-1-propinyl)-beta-carboline-3-carboxylic-acid-ethylester together with 50 ml of ethanol and 10 ml of semi-concentrated sulfuric acid is heated in the steam bath for 10 minutes. After the mixture is diluted with water, it is made alkaline with 2N sodium hydroxide and shaken twice with 50 ml of chloroform. The combined organic phases are dried, filtered and concentrated. The residue is separated by means of 65 g of silica gel with chloroform/ethanol (10/2) as the eluant. By consolidating the fractions and recrystallizing from ethanol, 400 mg of 6-(3-hydroxy-1-propinyl)-beta-carboline-3-carboxylic-acid-ethylester with a m.p. of 270°–275° C. is obtained.

EXAMPLE 40

The following compounds were prepared in the same manner:
5-(3-hydroxy-1-propinyl)-beta-carboline-3-carboxylic-acid-ethylester, m.p. 268°–270° C., decomposition); and
6-(3-hydroxy-1-propinyl)-4-methyl-beta-carboline-3-carboxylic-acid-ethylester, m.p. 211°–212° C. (alcohol/petroleum ether).

EXAMPLE 41

300 mg of 6-(3-hydroxy-1-propinyl)-beta-carboline-3-carboxylic-acid-ethylester is suspended in 25 ml of chloroform and 25 ml of acetone and mixed with 1.4 g of manganese dioxide. After stirring for 4 h, manganese dioxide is added again in an amount of 0.4 g. After standing overnight, 0.4 g of manganese dioxide is added again and the mixture is stirred for 8 h. Then it is filtered and the manganese dioxide is extracted in an Soxhlet extractor under acetone. After consolidating the filtrates, 150 mg of 6-(3-oxo-1-propinyl)-beta-carboline-3-carboxylic-acid-ethylester is obtained.

(M.p. exceeds 300° C.).

EXAMPLE 42

78 mg of 6-(3-hydroxy-1-propinyl)-beta-carboline-3-carboxylic-acid-ethylester in 2 ml of thionyl chloride is stirred for 3 h at room temperature. After evaporating till dry, the mixture is heated in ethanol and evacuated. By recrystallization from acetic-acid/cyclohexane, 40 mg of 6-(3-chloro-1-propinyl)-beta-carboline-3-carboxylic-acid-ethylester is obtained.

(M.p. 298° C., decomposition).

EXAMPLE 43

156 mg of 6-(3-chloro-1-propinyl)-beta-carboline-3-carboxylic-acid-ethylester is stirred together with 85 mg of piperidine and 76 mg of 1.5-diazabicyclo-[5.4.0]undec-5-ene in 10 ml of absolute ethanol under nitrogen and exclusion of water for 1½ h at 60° C. After evaporation, the residue is chromatographed on 25 g of silica gel with methylene-chloride/methanol (10/2) as the eluant. 51 mg of 6-[3-(1-piperidinyl)-1-propinyl]-beta-carboline-3-carboxylic-acid-ethylester is obtained.

(M.p. 215°-217° C.).

EXAMPLE 44

460 mg of 6-(3-chloro-1-propinyl)-beta-carboline-3-carboxylic-acid-ethylester is stirred in 4 ml of triethylphosphite for 3 h at 120°-130° C. The mixture, after being cooled, is thoroughly stirred with ether and the ether-soluble part is chromatographed after evaporation on 50 g of silica gel using methylene-chloride/ethanol (10/2). 105 mg of 6-[3-diethoxyphosphoryl-1-propinyl]-beta-carboline-3-carboxylic-acid-ethylester is obtained in the form of an oil.

EXAMPLE 45

383 mg of 6-amino-beta-carboline-3-carboxylic-acid-ethylester in 15 ml of ethanol is heated together with 0.58 ml of ethyldiisopropylamine and 0.18 ml of 1,4-dibromobutane for 6 h under nitrogen at the reflux. This is followed by an addition of 0.4 ml of 1,4-dibromobutane and reflux for 3 h. After evaporation, the mixture is washed with water and boiled with ethanol. 128 mg of 6-(1-pyrrolidinyl)-beta-carboline-3-carboxylic-acid-ethylester with a m.p. of 259°-261° C. is obtained.

EXAMPLE 46

The compounds below were prepared in similar manner:
4-methyl-6-(1-pyrrolidinyl)-beta-carboline-3-carboxylic-acid-ethylester, m.p. 244°-251° C.;
4-methoxymethyl-6-(1-pyrrolidinyl)-beta-carboline-3-carboxylic-acid-ethylester, m.p. 212°-214° C.; and
4-ethyl-6-(1-pyrrolidinyl)-beta-carboline-3-carboxylic-acid-ethylester, m.p. 205°-218° C.

EXAMPLE 47

3.25 g of 6-amino-4-methyl-beta-carboline-3-carboxylic-acid-ethylester in 70 ml of ethanol, together with 1.7 ml of 1,4-dichloro-2-cis-butene and 4.5 g of ethyldiisopropylamine is heated for 10 h at 50° C. After stirring in 250 ml of ice water, the precipitate is filtered, washed and dried in vacuum. The raw product (3.4 g of a mixture of dihydropyrrole derivative and pyrrole derivative) is dissolved in 600 ml of methylene chloride and, after addition of 17 g of pyrolusite, is stirred for 2 h at room temperature. After filtering, and distilling off the solvent, 2.75 g of raw product is obtained crystallizing out of acetone. In this manner, 2.13 g of 4-methyl-6-(1-pyrrolyl)-beta-carboline-3-carboxylic-acid-ethylester with a m.p. of 214°-217° C. is obtained.

EXAMPLE 48

446 mg of 6-amino-beta-carboline-3-carboxylic-acid-ethylester in 17.5 ml of absolute ethanol is heated together with 410 mg of 1.5-dibromopentane and 500 mg of ethyldiisopropylamine under nitrogen for 4 h at the reflux. After adding 74 mg more of 1,5-dibromopentane, boiling proceeds for another 2 h at the reflux. After evaporation, the remainder is introduced in methylene chloride, washed with saturated bicarbonate solution as well as with saturated NaCl solution, filtered and concentrated. After recrystallizing in alcohol, ethyl acetate and a little ether, 255 mg of 6-(1-piperidinyl)-beta-carboline-3-carboxylic-acid-ethylester, m.p. 255°-256° C., is obtained.

EXAMPLE 49

The following compounds were prepared in similar manner:
4-methyl-6-(1-piperidinyl)-beta-carboline-3-carboxylic-acid-ethylester, m.p. 215°-224° C.;
4-methoxymethyl-6-(1-piperidinyl)-beta-carboline-3-carboxylic-acid-ethylester, m.p. 163°-166° C.;
5-(1-piperidinyl)-beta-carboline-3-carboxylic-acid-ethylester, m.p. 274°-276° C.;
6-hexamethylenimino-beta-carboline-3-carboxylic-acid-ethylester, m.p. 220° C.; and
6-hexamethyleneimino-4-methyl-beta-carboline-3-carboxylic-acid-ethylester, m.p. 179° C.

EXAMPLE 50

510 mg of 6-amino-carboline-3-carboxylic-acid-ethylester in 7 ml of absolute tetrahydrofuran is heated together with 0.3 ml of 1,5-diaza-[5.4.0]-bicycloundec-5-ene and 240 mg of allyl bromide for ½ h under nitrogen at 60° C. Then the mixture is evaporated and distributed between ethyl acetate/water. The organic phase is dried, filtered and concentrated. The residue is chromatographed by means of 60 g of silica gel with methylene-chloride/ethanol (10/2) as the eluant. The more polar of the products generated is once more separated by means of 60 g of silica gel with methylene-chloride/ethanol (9/1) as the eluant. 200 mg of 6-N-allylamino-beta-carboline-3-carboxylic-acid-ethylester is isolated. M.p. 190°-194° C.

EXAMPLE 51

The following compounds were prepared in a similar manner:
5-allylamino-beta-carboline-3-carboxylic-acid-ethylester;
6-benzylamino-beta-carboline-3-carboxylic-acid-ethylester; and
6-N-allyl-4-methoxymethyl-3-carboxylic-acid-ethylester.

EXAMPLE 52

93 mg of 6-(N-ethylamino)-beta-carboline-3-carboxylic-acid-ethylester in 8 ml of absolute ethanol is heated together with 49 mg of 1,5-diaza-[5.4.0]bicycloundec-5-ene and 50 mg of allyl bromide under nitrogen for 2 h at 70° C. After evaporation, the substance is distributed in ethyl acetate and saturated sodium bicarbonate solution. The organic phase is dried, filtered and concentrated. The residue is chromatographed by means of 80 g of silica gel with methylene-chloride/ethanol (12/1) as the eluant, and, after recrystallizing out of ethylacetate/ether, 56 mg of 6-(N-allyl-N-ethylamino)-beta-carboline-3-carboxylic-acid-ethylester is obtained (m.p. 190°–192° C.).

EXAMPLE 53

The following compounds are prepared in similar manner:
6-(N-allyl-N-benzylamino)-beta-carboline-3-carboxylic-acid-ethylester;
6-(N-allyl-N-methylenecarboxyethylamino)-beta-carboline-3-carboxylic-acid-ethylester, m.p. 156°–158° C.; and
6-[N-allyl-N(2,2-diethoxyethyl)amino]-beta-carboline-3-carboxylic-acid-ethylester, m.p. 166°–167° C.

EXAMPLE 54

5.5 g of 6-amino-beta-carboline-3-carboxylic-acid-ethylester in 150 ml of absolute ethanol, together with 4.68 ml of allyl bromide and 6 ml of diazabicyclo-[5.4.0]undec-5-ene is stirred at 70° C. for 2½ h under nitrogen and excluding water. After adding 0.5 ml of allyl bromide, the mixture is once again heated to 70° C. for 30 minutes. After the ethanol is distilled off, the mixture is distributed in ethyl-acetate/saturated-bicarbonate-solution. The organic phase is washed with a saturated NaCl solution, dried, filtered and concentrated. After recrystallizing from ethyl acetate, 3.45 g of 6-(N,N-diallylamino)-beta-carboline-3-carboxylic-acid-ethylester, m.p. 194°–196° C., is obtained.

EXAMPLE 55

The following compounds are prepared in similar manner:
60(N,N-diallylamino)-4-methyl-beta-carboline-3-carboxylic-acid-ethylester, m.p. 158°–159° C. (ethyl aoetate);
6-(N,N-diallylamino)-4-ethyl-beta-carboline-3-carboxylic-acid-ethylester;
6-(N,N-diallylamino)-4-methoxymethyl-beta-carboline-3-carboxylic-acid-ethylester, (oil);
6-[N,N-di(2-butene-1-yl)-amino]-beta-carboline-3-carboxylic-acid-ethylester, m.p. 145° C. (ethylacetate/ether);
6-[N,N-di-(2-methyl-2-propene-1-yl)-amino]beta-carboline-3-carboxylic-acid-ethylester, m.p. 211°–212° C. (EtOH/petroleum-ether);
6-(N,N-diproparglyamino)-beta-carboline-3-carboxylic-acid-ethylester, m.p. 229°–230° C.;
6-(N,N-dibenzylamino)-beta-carboline-3-carboxylic-acid-ethylester, m.p. 200°–202° C.;
6-[N,N-di-(3-phenyl-2-propene-1-yl)-amino]-beta-carboline-3-carboxylic-acid-ethylester, m.p. 202°–203° C.;
6-[N,N-diallylamino]-4-methyl-beta-carboline-3-carboxylic-acid-propylester, m.p. 190°–192° C.; and
6-[N,N-diallylamino]-4-methyl-beta-carboline-3-carboxylic-acid-methylester, m.p. 146°–148° C.

EXAMPLE 56

255 mg of 6-amino-beta-carboline-3-carboxylic-acid-methylester, together with 183 mg of 2-bromo-acetic-acid-ethylester and 76 mg of potassium carbonate in a mixture of 2 ml of absolute dimethylformamide and 5 ml of absolute tetrahydrofuran, is stirred for 2 h at 40°–50° C. This substance is poured on ice and evacuated. The residue is thoroughly washed with water. The 60% yield is 6-[N-carboethoxy-methyleneamino]-beta-carboline-3-carboxylic-acid-ethylester with a m.p. of 157°–158° C.

EXAMPLE 57

150 mg of 6-N(5-bromopentanecarbonoyl)amino-beta-carboline-3-carboxylic-acid-ethylester in 3 ml of N-methyl-2-pyrrolidone is mixed with 10 mg of 80% sodium hydride and stirred overnight. After evaporation, the substance is neutralized with glacial acetic acid and triturated with water. The residue, after drying, is chromatographed on 30 g of silica gel with toluene/glacial-acetic-acid/water (10/10/1). 50 mg of 6-[2-piperidone-1-yl]-beta-carboline-3-carboxylic-acid-ethylester is obtained.

EXAMPLE 58

500 mg of 6-amino-beta-carboline-3-carboxylic-acid-ethylester in 15 ml of ethanol together with 0.92 ml of i-propylbromide and 0.63 ml of 1,5-diazabicyclo-[5.4.0]-undec-5-ene is heated for 8 h at 80° C. After evaporation, the substance is distributed in ethyl-acetate/-saturated-sodium-bicarbonate-solution. The organic phase is separated, dried, filtered and concentrated. The residue is chromatographed by means of 120 g of silica gel with methylene-chloride/ethanol (12/1) as the eluant. After recrystallization from ethanol/ether a 20% yield of 6-N-i-propylamino-beta-carboline-3-carboxylic-acid-ethylester with a m.p. 230°–232° C. is obtained.

EXAMPLE 59

The following compounds were prepared in a manner similar to example 56:
6-(N-[2-chloroethylamino])-beta-carboline-3-carboxylic-acid-ethylester, m.p. 165°–166° C. (ethyl-acetate/-petroleum-ether), and
6-(N-[2,2-diethoxyethylamine])-beta-carboline-3-carboxylic-acid-ethylester, m.p. 150°–151° C. (EtOH/-petroleum-ether).

EXAMPLE 60

1st stage

A solution of 21 g of indole-4-carboxylic-acid-methylester in 100 ml of methylene-chloride, 24.9 ml of triethylamine and 7.34 g of 4-dimethyl-aminopyridine is proportionately mixed at 0° C. with 34.2 g of p-toluene-sulfonic-acid-chloride. After 16 h at 0° C., the mixture is diluted with methylene chloride, washed neutral with saturated sodium bicarbonate solution and NaCl solution, and the solvent is distilled off in vacuum. 35.37 g of 1-tosylindole-4-carboxylic-acid-methylester with a m.p. of 145°–147° C. (diisopropylether) is obtained.

2nd stage

The suspension of 1.9 g of lithium-aluminum hydride in 165 ml of tetrahydrofuran cooled to 0° C. is proportionately mixed with 16.45 g of 1-tosylindole-4-carboxylic-acid-methylester. After 30 minutes 1.9 ml of water, 1.9 ml of 15% soda lye and 5.7 ml of water are carefully and sequentially dripped in. After 20 minutes, the precipitate is filtered off, washed out with acetic-acid-ethylester and the filtrates are concentrated. The raw product (15.97 g) is crystallized out of diisopropylether. 13.15 g of 4-hydroxymethyl-1-tosylindole with a m.p. of 125°–126° C. is obtained.

3rd stage

In sequence, 27 g of pulverulent potassium hydroxide, 27 ml of methyl iodide and 2.7 g of tetrabutyl-ammonium-hydrogen-sulfate are added to a solution of 13.5 g of 4-hydroxymethyl-1-tosylindole in 400 ml of methylene chloride. The substance is strongly agitated for 24 h. Then, it is filtered off of the potassium hydroxide, washed neutral with water, and the solvent is distilled off. The raw product (16.46 g) is crystallized out of diisopropylether. 12.2 g of 4-methoxymethyl-1-tosylindole with a m.p. of 85.5°–89° C. is obtained.

4th stage

A solution of 2.84 g of sodium in 155 ml of ethanol is dripped within 10 minutes into a solution of 15.57 g of 4-methoxymethyl-1-tosylindole in 155 ml of ethanol, whereupon the mixture is heated with reflux for 1½ h; next it is cooled, stirred into 1.5 liters of half-saturated ice-cold sodium-di-hydrogen-phosphate solution, extracted with ethyl acetate; whereupon, the ethyl-acetate extracts are washed neutral with water. After the solvent has been distilled off, the raw product is chromatographed on silical gel with hexane/ethyl-acetate (0–20%). 6.2 g of 4-methoxymethyl-indole is obtained in the form of a colorless oil.

5th and 6th stages

A solution of 4.25 g of acetaldehydisopropylimine in 8.5 ml of toluene is dripped within 30 minutes into a solution of 6.2 g of 4-methoxymethylindole in 31 ml of glacial acetic acid at 10° C. After 36 h at 0°–5° C., the mixture is stirred into 50 ml of ice water and is extracted with toluene, the water phase under intensive ice cooling is alkalized with 5 ml of soda lye to a pH of 12. Ether is used for extraction. Semi-concentrated NaCl solution is used for washing and the solvent is distilled off in vacuum. The raw product (8.52 g) is directly used in the next stage.

The solution of 8.52 g of amine product from stage 5 in 425 ml of toluene and 3.84 ml of nitroacetic-acid-methylester is heated for 4 h to 80° C. while a slight flow of nitrogen passes through. The product, after cooling, is washed neutral with hydrochloric acid and water, the solvent is distilled off, and the raw product (9.33 g) is chromatographed on silica gel with hexane/ethyl-acetate (0–20%). 7.89 g of 4-methoxymethyl-indole-3-[2-nitro-3-methyl]-propionic-acid-ethylester is obtained in the form of a hard foam.

7th stage 8.08 g of 4-methoxymethylindole-3-[2-nitro-3-methyl]-propionic-acid-ethylester is hydrogenated in 320 ml of ethanol with 10 g of Raney nickel at 20 bar and room temperature. The hydrogen absorption is terminated after 60 minutes. The substance is filtered off the catalyst and the solvent is distilled off in vacuum at a bath temperature of 30° C. 6.4 g of 4-methoxymethylindole-3-[2-amino-3-methyl]-propionic-acid-ethylester is obtained in the form of a colorless oil.

8th stage 6.4 g of crude 4-methoxymethyl-3-[2-amino-3-methyl]-propionic-acid-ethylester is boiled with 0.66 g of paraformaldehyde in 140 ml of toluene for 16 h on a water separator. After cooling the mixture to 0° C., it is diluted with 140 ml of toluene, mixed with 11 g of dichlorodicyanobenzoquinone and stirred for 40 minutes. The substance is diluted with 500 ml of ethyl acetate, washed several times with diluted ammonia solution and then rinsed with water, dried, filtered, and the solvent is distilled off in vacuum. 4.81 g of raw product is obtained. By chromatography on silica gel with hexane/ethyl-acetate (50–100%) 1.78 g of 5-methoxymethyl-4-methyl-beta-carboline-3-carboxylic-acid-ethylester with a m.p. of 133°–135° C. (from ethyl acetate) is obtained.

EXAMPLE 61

As described in the stages 5–8, the compounds below are prepared from the corresponding indoles:
5-ethoxymethyl-4-methyl-beta-carboline-3-carboxylic-acid-ethylester, m.p. 134°–136° C. (ethyl acetate);
5-ethoxymethyl-4-methyl-beta-carboline-3-carboxylic-acid-methylester, m.p. 167°–170° C. (ethyl acetate);
5-benzyloxy-4-ethyl-beta-carboline-3-carboxylic-acid-ethylester, m.p. 192°–193° C. (ethyl acetate);
5-benzyloxy-4-methyl-beta-carboline-3-carboxylic-acid-ethylester, m.p. 190°–192° C. (ethyl acetate);
5-phenyloxy-4-methyl-beta-carboline-3-carboxylic-acid-ethylester; and
5-acetoxymethyl-4-methyl-beta-carboline-3-carboxylic-acid-ethylester.

EXAMPLE 62

476 mg of 6-amino-4-methoxymethyl-beta-carboline-3-carboxylic-acid-ethylester is mixed in 4.4 ml of dimethyl disulfide with 0.32 ml of i-amyl nitrite at room temperature under nitrogen and then heated for 20 minutes at 80° C. After evaporation, the substance is introduced into acetone and evacuated. The filtrate is chromatographed by means of 180 g of silica gel with toluene/glacial-acetic-acid/water (10/10/1) as the eluant. After recrystallizing the corresponding fractions from ethanol/petroleum-ether, 47 mg of 4-methoxy-methyl-6-thiomethyl-beta-carboline-3-carboxylic-acid-ethylester with a m.p. of 138°–139° C. is obtained.

EXAMPLE 63

138 microliters of 3-chloropropane-sulfonic-acid-chloride is dripped into 305 mg of 6-amino-4-methyl-beta-carboline-3-carboxylic-acid-ethylester in 10 ml of pyridine at room temperature. After 1 h, the substance is separated from the precipitate and concentrated. After tower-purification by means of silica-gel in the methanol/ethanol (10/1) system, 120 mg of 6-(3-chloropropane-sulfonamido)-4-methyl-beta-carboline-3-carboxylic-acid-ethylester with a m.p. of 217°–219° C. (decomposition) is obtained from petroleum ether.

EXAMPLE 64

87 mg of 3-chloro-propane-sulfonamido derivative and 6.5 mg of sodium-hydride/oil suspension (80%) are heated in 5 ml of absolute ethanol for 1 h at the reflux. After adding 25 microliters of glacial acetic acid, the substance is distilled and the residue is washed with water. 70 mg of 6-(1,1-dioxo-1,2-thiazolidine-2-yl)-4-methyl-beta-carboline-3-carboxylic-acid-ethylester with a m.p. of 230° C. is obtained.

EXAMPLE 65

390 mg of 5-chloro-6-amino-beta-carboline-3-carboxylic-acid-ethylester in 15 ml of ethanol together with 230 mg of 1,5-dioxanepentane and 310 mg of 1.8-diazabicyclo-[5.4.0]undec-7-ene is heated for 1½ h to boiling. After evaporation, the residue is chromatographed on silica gel with methylene-chloride/ethanol (10/1). 270 mg of 5-chloro-6-(1-piperidino)-beta-carboline-3-carboxylic-acid-ethylester with a m.p. of 245° C. (decomposition) is obtained.

EXAMPLE 66

420 mg of 5-chloro-6-nitro-beta-carboline-3-carboxylic-acid-ethylester, 40 mg of cuprous iodide and 130 mg of potassium benzylate in 8 ml of N-methylpyrrolidone are heated for 7 h at 70° C. After the solvent is distilled off, the residue is chromatographed on silica gel with toluene/glacial-acetic-acid/water (10/10/1). 280 mg of 5-benzyloxy-6-nitro-beta-carboline-3-carboxylic-acid-ethylester with a m.p. of 254° C. (dissociation) is obtained.

EXAMPLE 67

420 mg of 5-chloro-6-nitro-beta-carboline-3-carboxylic-acid-ethylester and 100 mg of piperidine in 10 ml of hexamethylphosphorotriamide are heated for 2 h to 80° C. After the solvent is distilled off, the residue is chromatographed on silica gel with methylene-chloride/ethanol. 350 mg of 5-piperidino-6-nitro-beta-carboline-3-carboxylic-acid-ethylester with a m.p. of 307° C. (decomposition) is obtained.

EXAMPLE 68

140 mg of 5-piperidino-6-nitro-beta-carboline-3-carboxylic-acid-ethylester in 10 ml of tetrahydrofuran is mixed with the four-fold molar amount of titanium trichloride in water. After 6 minutes, the substance is neutralized, filtered and evaporated. The residue is extracted with methylene chloride, and the extracts are concentrated and recrystallized from glacial acetic acid. 102 mg of 5-piperidino-6-amino-beta-carboline-3-carboxylic-acid-ethylester with a m.p. of 188°-190° C. is obtained.

EXAMPLE 69

6.8 g of imidazole is dissolved in 75 ml of dry tetrahydrofuran (solution A). 1.8 ml of thionyl chloride is dissolved in 25 ml of dry tetrahydrofuran (solution B).

B is dripped into A. After stirring for 1 h, the reaction mixture is filtered and the residue is washed with 25 ml of tetrahyrofuran. The filtrate is added dropwise into a stirred suspension of 2.5 g of beta-carboline-3-carboxylic-acid in 100 ml of dimethylformamide. The reaction mixture is allowed to stand overnight at room temperature with exclusion of water (E).

2.3 g of sodium is dissolved in 40 ml of methanol (C). 8.0 g of hydroxylamino-hydrochloride is dissolved in 100 ml of methanol (D). D is added to C while stirring. The precipitate is filtered off, and 6.0 g of freshly distilled ethyl-carbonitrile is added dropwise to the filtrate. The reaction mixture is allowed to stand for two days at room temperature with water exclusion. (F)

The reaction mixture F is concentrated in vacuum. After adding 50 ml of toluene, the solvent is again evacuated in vacuum. The residue is heated for about 5 minutes in a steam bath, and a strongly exothermal reaction takes place. The moment the reaction is terminated, the solution is added to E. The reaction mixture is stirred for 2 h at room temperature and allowed to stand overnight at room temperature. The reaction mixture then is concentrated in vacuum. After adding 200 ml of toluene, the reaction mixture is boiled for 3 h at the reflux. The hot reaction mixture then is filtered. After evaporating the filtrate, a residue is obtained to which is added 20 ml of water. The residue is filtered and washed with water and ether. After recrystallization from 15 ml of n-butanol, there is obtained 1.5 g of 3-(5'-ethyl-1',2',4'-oxadiazole)-yl)-beta-carboline with a m.p. of 257°-260° C.

EXAMPLE 70

A mixture of 2.4 g of 3-cyano-beta-carboline, 1.1 g of hydroxylamine-hydrochloride, 200 ml of 99% ethanol and 5.2 ml of a potassium carbonate solution (2.2 g of potassium carbonate in 10 ml of water) is boiled in an oil bath at 90° C. outside temperature for 22 h at the reflux. The reaction mixture is filtered hot. The filtrate is concentrated. The residue is treated with 100 ml of water. The precipitate is filtered off, washed with water and dried in air. 2.4 g of beta-carboline-3-carboxylic-acid-amide-oxime with a m.p. of 159°-163° C. is obtained.

A mixture of 1.2 g of beta-carboline-3-carboxylic-acid-amidoxime and 10 ml of freshly distilled propionic-acid anhydride is stirred for 2 h at room temperature and thereafter for 5 h in an oil bath at 120° C. outside temperature. The reaction mixture is allowed to stand overnight at room temperature and then is concentrated. After adding 100 ml of tetrahydrofuran, the reaction mixture is saturated with gaseous methylamine. After being allowed to stand overnight at room temperature, the reaction mixture is concentrated, treated with methylene chloride and filtered. The filtrate is concentrated and again treated with ethyl acetate. 0.4 g of 3-(3'-(5'-ethyl-1',2',4'-oxadiazole)-yl)-beta-carboline with a m.p. of 214°-216° C. is obtained.

The following compounds were prepared in similar manner:

6-bromo-3-(5'-(3'-methyl-1',2',4'-oxadiazole)-yl)-beta-carboline, m.p. 353°-358° C. (decomposition);
3-(5'-(3'-ethyl-1',2',4'-oxadiazole)-yl)-beta-carboline, m.p. 245°-251° C.;
4-ethyl-3-(5'-(3'-methyl-1',2',4'-oxadiazole)-yl)-beta-carboline, m.p. 266°-268° C.;
3-(5'-(3'-propyl-1',2',4'-oxadiazole)-yl)-beta-carboline, m.p. 187°-208° C.;
3-(5'-(3'-butyl-1',2',4'-oxadiazole)-yl)-beta-carboline, m.p. 208°-211° C.;
3-(5'-(3'-ethyl-1',2',4'-oxadiazole)-yl)-6-piperidino-beta-carboline, m.p. 152°-170° C.;
3-(5'-(3'-isopropyl-1',2',4'-oxadiazole)-yl)-beta-carboline, m.p. 220°-225° C.;
6-diallylamino-3-(5'-(3'-methyl-1',2',4'-oxadiazole)-yl)-beta-carboline, (decomposition);
6-diproparglyamino-3-(5'-(3'-ethyl-1',2',4'-oxadiazole)-yl)-beta-carboline, m.p. 217°-220° C.;
6-diallylamino-3-(5'-(3'-ethyl-1',2',4'-oxadiazole)-yl)-beta-carboline, m.p. 181°-186° C.;
3-(5'-(3'-allyl-1',2',4'-oxadiazole)-yl)-beta-carboline, m.p. 194°-205° C.;
4-ethyl-3(5'-(3'-ethyl'1',2',4'-oxadiazole)-yl)-beta-carboline, m.p. 235°-240° C.;

3-(5'-(3'-methoxymethyl-1',2',4'-oxadiazole)-yl)-beta-carboline, m.p. 220°–229° C.;

6-diallylamino-3-(5'-(3'-ethyl-1',2',4'-oxadiazole)-yl)-4-methyl-beta-carboline, m.p. 154°–160° C.

3-(5'-(3'-cyclopropyl-1',2',4'-oxadiazole)-yl)-beta-carboline, m.p. 241°–243° C.;

3-(5'-(3'-allyl-1',2',4'-oxadiazole)-yl)-6-diallyl-amino-beta-carboline, m.p. 168°–193° C.;

3-(3'-(5'-methyl-1',2',4'-oxadiazole)-yl)-beta-carboline, m.p. 279°–287° C.;

3-(3'-(5'-ethyl-1',2',4'-oxadiazole)-yl)-beta-carboline, m.p. 214°–216° C.; and 3-(3'-(5'-propyl-1',2',4'-oxadiazole)-yl)-beta-carboline, m.p. 195°–197° C.

EXAMPLE 71

A solution of 16 ml of thionyldiimidazole in 20 ml of tetrahydrofuran is added dropwise to a suspension of 445 mg (1.2 mmol) of 5-benzyloxy-4-methoxymethyl-$\beta$-carbolin-3-carbonic acid in 10 ml of dimethyl formamide. (The free $\beta$-carboline-3-carbonic acid was prepared by acid hydrolysis of the corresponding $\beta$-carboline-3-carbonic acid ethylester). After stirring for 2 hours, 1.0 g (12 mmol) of propionamidoxime is added to the reaction mixture. After stirring for 1 hour, the reaction mixture is evaporated, 40 ml of toluene is added and the mixture is heated for 4 hours in an oil-bath at 110° C. After cooling, the toluene phase is decanted, evaporated and treated with a few milliliters of ether. The ether phase is removed and the residue dissolved in a few milliliters of hot ethanol. An equal amount of water is added and the precipitate is filtered after crystallization.

142 mg of 5-benzyloxy-3-(3-ethyl-1,2,4-oxadiazol-5-yl)-4-methoxymethyl-$\beta$-carboline is obtained.

m.p. 180°–184° C.

IR: 3370, 1600 cm$^{-1}$.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A beta-carboline of the formula

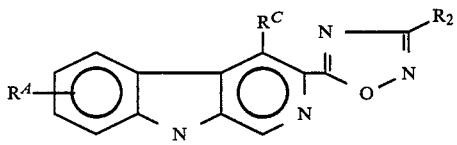

wherein $R^A$ is H, F, Cl, Br, I, $NO_2$, CN, $CF_3$, $SCH_3$, $NR^{16}R^{17}$ or $NHCOR^{16}$, wherein $R^{16}$ and $R^{17}$ are the same or different and each is hydrogen or alkenyl or alkynyl each of up to 6 C-atoms, or aralkyl of up to 10 C-atoms, or $R^A$ is $OR^{18}$ wherein $R^{18}$ is benzyl and wherein each compound may contain 1–4 identical or different non-H $R^A$ groups;

$R^C$ is hydrogen, lower alkyl, alkoxyalkyl of up to 6 C-atoms, or cycloalkyl of 3–6 C-atoms and $R^2$ is 3-allyl, $C_{1-4}$-alkyl, cyclopropyl or methoxymethyl.

2. 5-benzyloxy-3-(3-ethyl-1,2,4-oxadiazol-5-yl)-4-methoxymethyl-$\beta$-carboline, a compound of claim 1.

3. A compound of claim 1, wherein $R^A$ is H in all positions.

4. 3-(3'-(5'-ethyl-1',2',4'-oxadiazole)-yl)-beta-carboline, a compound of claim 1.

5. 6-bromo-3-(5'-(3'-methyl-1',2',4'-oxadiazole)-yl)-beta-carboline, a compound of claim 1.

6. 3-(5'-(3'-ethyl-1',2',4'-oxadiazole)-yl)-beta-carboline, a compound of claim 1.

7. 4-ethyl-3-(5'-(3'-methyl-1',2',4'-oxadiazole)-yl)-beta-carboline, a compound of claim 1.

8. 3-(5'-(3'-propyl-1',2',4'-oxadiazole)-yl)-beta-carboline, a compound of claim 1.

9. 3-(5'-(3'-butyl-1',2',4'-oxadiazole)-yl)-beta-carboline, a compound of claim 1.

10. 3-(5'-(3'-ethyl-1',2',4'-oxadiazole)-yl)-6-piperidino-beta-carboline, a compound of claim 1.

11. 3-(5'-(3'-isopropyl-1',2',4'-oxadiazole)-yl)-beta-carboline, a compound of claim 1.

12. 6-diallylamino-3-(5'-(3'-methyl-1',2',4'-oxadiazole)-yl)-beta-carboline, a compound of claim 1.

13. 6-dipropargylamino-3-(5'-(3'-ethyl-1',2',4'-oxadiazole)-yl)-beta-carboline, a compound of claim 1.

14. 6-diallylamino-3-(5'-(3'-ethyl-1',2',4'-oxadiazole)-yl)-beta-carboline, a compound of claim 1.

15. 3-(5'-(3'-allyl-1',2',4'-oxadiazole)-yl)-beta-carboline, a compound of claim 1.

16. 4-ethyl-3(5'-(3'-ethyl-1',2',4'-oxadiazole)-yl)-beta-carboline, a compound of claim 1.

17. 3-(5'-(3'-methoxymethyl-1',2',4'-oxadiazole)-yl)-beta-carboline, a compound of claim 1.

18. 6-diallylamino-3-(5'-(3'-ethyl-1',2',4'-oxadiazole-yl)-4-methyl-beta-carboline, a compound of claim 1.

19. 3-(5'-(3'-cyclopropyl-1',2',4'-oxadiazole)-yl)-beta-carboline, a compound of claim 1.

20. 3-(5'-(3'-allyl-1',2',4'-oxadiazole)-yl)-6-diallyl-amino-beta-carboline, a compound of claim 1.

21. 3-(3'-(5'-methyl-1',2',4'-oxadiazole)-yl)-beta-carboline, a compound of claim 1.

22. 3-(3'-(5'-ethyl-1',2'4'-oxadiazole)-yl)-beta-carboline, a compound of claim 1.

23. 3-(3'-(5'-propyl-1',2',4'-oxadiazole)-yl)-beta-carboline, a compound of claim 1.

24. A pharmaceutical composition comprising an amount of a compound of claim 1, effective as a tranquilizer and a pharmaceutically acceptable carrier.

25. A pharmaceutical composition of claim 24 wherein the tranquilizing amount of active ingredient is 0.02 to 10 mg.

26. A method of achieving a tranquilizing effect in a patient in need of such treatment which comprises administering to the patient an amount of a compound of claim 1, effective as a tranquilizer.

* * * * *